US011894105B2

United States Patent
Gottimukkala et al.

(10) Patent No.: US 11,894,105 B2
(45) Date of Patent: Feb. 6, 2024

(54) METHODS FOR DETECTION OF FUSIONS USING COMPRESSED MOLECULAR TAGGED NUCLEIC ACID

(71) Applicant: LIFE TECHNOLOGIES CORPORATION, Carlsbad, CA (US)

(72) Inventors: Rajesh Gottimukkala, Fremont, CA (US); Cheng-Zong Bai, Taipei (TW); Dumitru Brinza, Montara, CA (US); Jeoffrey Schageman, Austin, TX (US); Varun Bagai, Austin, TX (US)

(73) Assignee: Life Technologies Corporation, Carlsbad, CA (US)

( * ) Notice: Subject to any disclaimer, the term of this patent is extended or adjusted under 35 U.S.C. 154(b) by 195 days.

(21) Appl. No.: 16/136,463

(22) Filed: Sep. 20, 2018

(65) Prior Publication Data

US 2019/0087539 A1 Mar. 21, 2019

Related U.S. Application Data

(60) Provisional application No. 62/560,745, filed on Sep. 20, 2017.

(51) Int. Cl.
*G16B 30/00* (2019.01)
*C12Q 1/6853* (2018.01)
*G16B 30/10* (2019.01)
*G16B 20/20* (2019.01)
*G16B 50/50* (2019.01)

(52) U.S. Cl.
CPC ........... *G16B 30/00* (2019.02); *C12Q 1/6853* (2013.01); *G16B 20/20* (2019.02); *G16B 30/10* (2019.02); *G16B 50/50* (2019.02)

(58) Field of Classification Search
CPC ...... C12Q 1/6853; G16B 20/20; G16B 30/00; G16B 30/10; G16B 50/50
See application file for complete search history.

(56) References Cited

U.S. PATENT DOCUMENTS

2012/0197623 A1 8/2012 Homer et al.

FOREIGN PATENT DOCUMENTS

WO WO-2015177570 A1 11/2015
WO WO-2016011378 A1 1/2016

OTHER PUBLICATIONS

Behind the Bench Staff, ThermoFisher Scientific, Aug. 29, 2014, The Ion AmpliSeq RNA Lung Cancer Research Fusion Panel, https://www.thermofisher.com/blog/behindthebench/the-ion-ampliseq-rna-lung-cancer-research-fusion-panel/ (Year: 2014).*
Alcaide, M., et al.., 2017. Targeted error-suppressed quantification of circulating tumor DNA using semi-degenerate barcoded adapters and biotinylated baits. Scientific Reports, 7(1), pp. 1-19. (Year: 2017).*
Lysholm, F., Andersson, B. and Persson, B., 2011. FAAST: Flow-space assisted alignment search tool. BMC bioinformatics, 12(1), pp. 1-7. (Year: 2011).*
Ion Reporter, ThermoFisher Scientific, 5.0 Software User Guide, MAN0013516 A.0, Jan. 12, 2016, p. 1-406 (Year: 2016).*
Hovelson, D.H., et al., 2015. Development and validation of a scalable next-generation sequencing system for assessing relevant somatic variants in solid tumors. Neoplasia, 17(4), pp. 385-399. (Year: 2015).*
Hovelson, D.H., et al., 2015. Development and validation of a scalable next-generation sequencing system for assessing relevant somatic variants in solid tumors. Neoplasia, 17(4), Supplemental Information , p. 1-82. (Year: 2015).*
Torres-García, W., Zheng, S., Sivachenko, A., Vegesna, R., Wang, Q., Yao, R., Berger, M.F., Weinstein, J.N., Getz, G. and Verhaak, R.G., 2014. PRADA: pipeline for RNA sequencing data analysis. Bioinformatics, 30(15), pp. 2224-2226. (Year: 2014).*
Alcaide, M., et al.., 2017. Targeted error-suppressed quantification of circulating tumor DNA using semi-degenerate barcoded adapters and biotinylated baits. Scientific Reports, 7(1), Supplemental Information, pp. 1-12. (Year: 2017).*
Engreitz, J.M., Haines, J.E., Perez, E.M., Munson, G., Chen, J., Kane, M., McDonel, P.E., Guttman, M. and Lander, E.S., 2016. Local regulation of gene expression by lncRNA promoters, transcription and splicing. Nature, 539(7629), pp. 452-455. (Year: 2016).*
Sakarya, O., Breu, H., Radovich, M., Chen, Y., Wang, Y.N., Barbacioru, C., Utiramerur, S., Whitley, P.P., Brockman, J.P., Vatta, P. and Zhang, Z. RNA-Seq mapping and detection of gene fusions with a suffix array algorithm. PLoS computational biology, 8(4), p.e1002464. p. 1-10. (Year: 2012).*
Sakarya, O., Breu, H., Radovich, M., Chen, Y., Wang, Y.N., Barbacioru, C., Utiramerur, S., Whitley, P.P., Brockman, J.P., Vatta, P. and Zhang, Z. RNA-Seq mapping and detection of gene fusions with a suffix array algorithm. PLoS computational biology, 8(4), p. e1002464. Supplementary Methods, p. 1-26. (Year: 2012).*

(Continued)

*Primary Examiner* — Olivia M. Wise
*Assistant Examiner* — Janna Nicole Schultzhaus
(74) *Attorney, Agent, or Firm* — Carolyn Koenig

(57) ABSTRACT

A method for compressing nucleic acid sequence data wherein each sequence read is associated with a molecular tag sequence, wherein a portion of the sequence reads alignments correspond to sequence reads mapped to a targeted fusion reference sequence includes determining a consensus sequence read for each family of sequence reads based on flow space signal measurements corresponding to the family of sequence reads, determining a consensus sequence alignment for each family of sequence reads, wherein a portion of the consensus sequence alignments correspond to the consensus sequence reads aligned with the targeted fusion reference sequence, generating a compressed data structure comprising consensus compressed data, the consensus compressed data including the consensus sequence read and the consensus sequence alignment for each family, and detecting a fusion using the consensus sequence reads and the consensus sequence alignments from the compressed data structure.

20 Claims, 8 Drawing Sheets
Specification includes a Sequence Listing.

(56) References Cited

OTHER PUBLICATIONS

Cai, X., Janku, F., Zhan, Q. and Fan, J.B. Accessing genetic information with liquid biopsies. Trends in Genetics, 31(10), pp. 564-575. (Year: 2015).*
Brandon M. C et al: "Data structures and compression algorithms for genomic sequence data", Bio Informati CS, vol. 25, No. 14, Jul. 15, 2009 (Jul. 15, 2009), pp. 1731-1738, XP055025034.
Carol Beadling et al: "A Multiplexed Amplicon Approach for Detecting Gene Fusions by Next-Generation Sequencing", Journal of Molecular Diagnostics, The, vol. 18, No. 2, Mar. 1, 2016 (Mar. 1, 2016), pp. 165-175, XP055504605.
Cheng Kin-On et al: "Compressing population DNA sequences using multiple reference sequences", 2017 Asia-Pacific Signal and Information Processing Association Annual Summit and Conference (APSIPA ASC), IEEE, Dec. 12, 2017 (Dec. 12, 2017), pp. 760-764, XP033315522.
Daniel L. Cameron et al: "GRIDSS: sensitive and specific genomic rearrangement detection using positional de Bruijn graph assembly", Genome Research, vol. 27, No. 12, Nov. 2, 2017 (Nov. 2, 2017), pp. 2050-2060, XP055522516.
Edgren, H et al., "Identification of fusion genes in breast cancer by paired-end RNA-sequencing" Genome Biology, Biomed Central, Ltd., London, GB, vol. 12, No. 1, Jan. 19, 2011, 14 pp.
Gillian Hsieh et al: "Statistical algorithms improve accuracy of gene fusion detection", Nucleic Acids Research, vol. 45, No. 13, May 24, 2017 (May 24, 2017), pp. e126-e126, XP055504277. p. 1-11.
International Search Report and Written Opinion PCT/US2018/051872, 18 pages, dated Nov. 30, 2018.
Jian Zhao et al: "GFusion: an Effective Algorithm to Identify Fusion Genes from Cancer RNA-Seq Data", Scientific Reports, vol. 7, No. 1, Jul. 31, 2017 (Jul. 31, 2017), XP055522396. p. 1-12.
Jones D.C et al: "Compression of next-generation sequencing reads aided by highly efficient de novo assembly", Nucleic Acids Research, vol. 40, No. 22, Dec. 1, 2012 (Dec. 1, 2012), pp. e171-e171, XP055330945. p. 1-9.
Latysheva N.S., et al: "Discovering and understanding oncogenic gene fusions through data intensive computational approaches", Nucleic Acids Research, vol. 44, No. 10, Apr. 21, 2016 (Apr. 21, 2016), pp. 4487-4503, XP055522214.
"Mertens, Fredrik et al., "The emerging complexity of gene fusions in cancer", NatureReviews, Cancer, vol. 15, No. 6, Jun. 1, 2015, 371-381".
Neerav N. Shukla: "Plasma DNA-Based Molecular Diagnosis, Prognostication, and Monitoring of Patients With EWSR1 Fusion-Positive Sarcomas", May 23, 2017 (May 23, 2017), pp. 1-11, XP055522515, Retrieved from the Internet: URL:http://ascopubs.org/doi/pdfdirect/10.1200/P0.16.00028 [retrieved on Nov. 9, 2018].
Wang Q et al: "Application of next generation sequencing to human gene fusion detection: computational tools, features and perspectives", Briefings in Bioinformatics., vol. 14, No. 4, Aug. 9, 2012 (Aug. 9, 2012) , pp. 506-519, XP055522754.
Yoshihara K et al: "The landscape and therapeutic relevance of cancer-associated transcript fusions", Oncogene, vol. 34, No. 37, Dec. 15, 2014 (Dec. 15, 2014), pp. 4845-4854, XP055523094.

* cited by examiner

SEQUENCE LISTING

<160> NUMBER OF SEQ ID NOS: 1

<210> SEQ ID NO 1
<211> LENGTH: 100
<212> TYPE: DNA
<213> ORGANISM: Artificial Sequence
<220> FEATURE:
<223> OTHER INFORMATION: Description of Artificial Sequence: Ordering of
      Nucleotide Species Flows

<400> SEQUENCE: 1
tacgtacgtc tgagcatcga tcgatgtaca gctacgtacg tctgagcatc gatcgatgta      60
cagctacgta cgtctgagca tcgatcgatg tacagctacg                           100

METHODS FOR DETECTION OF FUSIONS USING COMPRESSED MOLECULAR TAGGED NUCLEIC ACID

CROSS-REFERENCE

This application claims the benefit under 35 U.S.C. § 119(e) of U.S. Provisional Application No. 62/560,745, filed Sep. 20, 2017. The entire content of the aforementioned application is incorporated by reference herein.

SEQUENCE LISTING

The instant application contains a Sequence Listing which has been submitted electronically in ASCII format and is hereby incorporated by reference in its entirety. Said ASCII copy, created on Mar. 9, 2022, is named LT01291_ST25.txt and is 802 bytes in size.

BRIEF SUMMARY OF THE INVENTION

Structural variants, such as large scale deletions, insertions, inversions, genomic rearrangements, gene fusions, and the like, can be associated with various genetic disorders and cancers. Structural variants can often lead to significant disruptions in the production of proteins essential for the proper function of a cell. For example, genomic rearrangements and gene fusions can lead to mRNA coding for chimeric proteins, having a first part from one protein and a second part from another protein. Often, these chimeric proteins no longer function like either the first or second protein and can lead to disruption of regularity pathways. In cancer cells, the disrupted regulatory pathways may be involved in the regulation of apoptosis, cell growth, or the like and, as a result of the gene fusion, enable the cancer cells to grow unchecked.

Molecular tagging of nucleic acid sequences is useful for identifying the nucleic acid sequence reads that originate from the same polynucleotide molecule, for example from a cell-free DNA (cfDNA) sample, and classifying them into a family based on their tag sequence. Large amounts of molecular tagged nucleic acid sequence data, obtained from a nucleic acid sample using various techniques, platforms or technologies, may be stored and processed for detection of fusions. There is a need for new methods, systems and computer readable media that compress molecular tagged nucleic acid sequence data to reduce memory requirements for storage and detect fusions in compressed molecular tagged nucleic acid sequence data, including that obtained from cfDNA samples.

According to an exemplary embodiment, there is provided a method for compressing molecular tagged nucleic acid sequence data for fusion detection, comprising (a) receiving a plurality of nucleic acid sequence reads and a plurality of sequence alignments for a plurality of families of sequence reads, wherein each sequence read is associated with a molecular tag sequence, the molecular tag sequence identifying a family of sequence reads resulting from a particular polynucleotide molecule in a nucleic acid sample, each family having a number of sequence reads, wherein a portion of the sequence alignments correspond to sequence reads mapped to a targeted fusion reference sequence; (b) determining a consensus sequence read for each family of sequence reads based on flow space signal measurements corresponding to the sequence reads for the family; (c) determining a consensus sequence alignment for each family of sequence reads, wherein a portion of the consensus sequence alignments correspond to the consensus sequence reads aligned with the targeted fusion reference sequence; (d) generating a compressed data structure comprising consensus compressed data, the consensus compressed data including the consensus sequence read and the consensus sequence alignment for each family; and (e) detecting a fusion using the consensus sequence reads and the consensus sequence alignments from the compressed data structure.

According to an exemplary embodiment, there is provided a non-transitory machine-readable storage medium comprising instructions which, when executed by a processor, cause the processor to perform a method for compressing molecular tagged nucleic acid sequence data for fusion detection, comprising (a) receiving a plurality of nucleic acid sequence reads and a plurality of sequence alignments for a plurality of families of sequence reads, wherein each sequence read is associated with a molecular tag sequence, the molecular tag sequence identifying a family of sequence reads resulting from a particular polynucleotide molecule in a nucleic acid sample, each family having a number of sequence reads, wherein a portion of the sequence alignments correspond to sequence reads mapped to a targeted fusion reference sequence; (b) determining a consensus sequence read for each family of sequence reads based on flow space signal measurements corresponding to the sequence reads for the family; (c) determining a consensus sequence alignment for each family of sequence reads, wherein a portion of the consensus sequence alignments correspond to the consensus sequence reads aligned with the targeted fusion reference sequence; (d) generating a compressed data structure comprising consensus compressed data, the consensus compressed data including the consensus sequence read and the consensus sequence alignment for each family; and (e) detecting a fusion using the consensus sequence reads and the consensus sequence alignments from the compressed data structure.

According to an exemplary embodiment, there is provided a system for compressing molecular tagged nucleic acid sequence data for fusion detection, comprising a machine-readable memory and a processor in communication with the memory, wherein the processor is configured to execute machine-readable instructions, which, when executed by the processor, cause the system to perform a method comprising (a) receiving a plurality of nucleic acid sequence reads and a plurality of sequence alignments for a plurality of families of sequence reads, wherein each sequence read is associated with a molecular tag sequence, the molecular tag sequence identifying a family of sequence reads resulting from a particular polynucleotide molecule in a nucleic acid sample, each family having a number of sequence reads, wherein a portion of the sequence alignments correspond to sequence reads mapped to a targeted fusion reference sequence; (b) determining a consensus sequence read for each family of sequence reads based on flow space signal measurements corresponding to the sequence reads for the family; (c) determining a consensus sequence alignment for each family of sequence reads, wherein a portion of the consensus sequence alignments correspond to the consensus sequence reads aligned with the targeted fusion reference sequence; (d) generating a compressed data structure comprising consensus compressed data, the consensus compressed data including the consensus sequence read and the consensus sequence alignment for each family; and (e) detecting a fusion using the consensus sequence reads and the consensus sequence alignments from the compressed data structure.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

FIG. 4 discloses SEQ ID NO: 1.

DETAILED DESCRIPTION OF THE INVENTION

Figure 1:
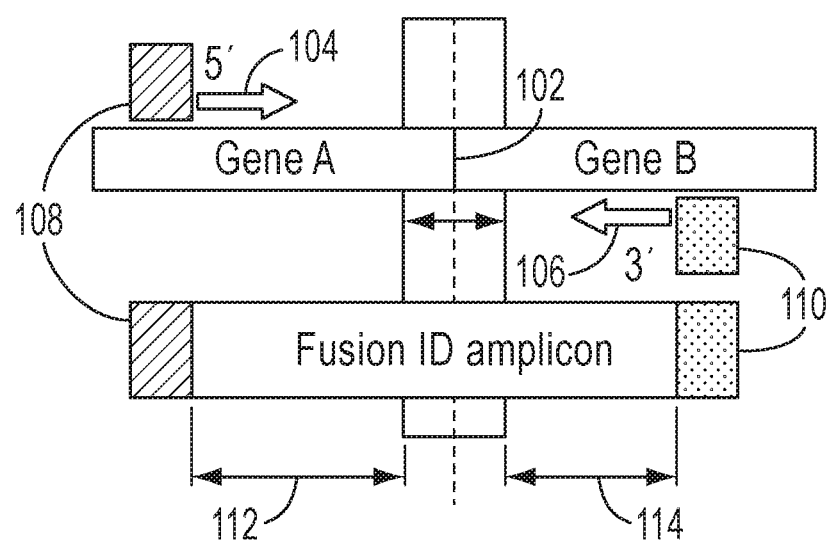
FIG. 1 illustrates an example of primer design for detection of fusions, where the primers have molecular tags, in accordance with an embodiment.

In accordance with the teachings and principles embodied in this application, new methods, systems and non-transitory machine-readable storage medium are provided to compress molecular tagged nucleic acid sequence data to form consensus compressed data for families of nucleic acid sequence reads associated with unique molecular tags and to detect fusions based on the consensus compressed data.

In various embodiments, DNA (deoxyribonucleic acid) may be referred to as a chain of nucleotides consisting of 4 types of nucleotides; A (adenine), T (thymine), C (cytosine), and G (guanine), and that RNA (ribonucleic acid) is comprised of 4 types of nucleotides; A, U (uracil), G, and C. Certain pairs of nucleotides specifically bind to one another in a complementary fashion (called complementary base pairing). That is, adenine (A) pairs with thymine (T) (in the case of RNA, however, adenine (A) pairs with uracil (U)), and cytosine (C) pairs with guanine (G). When a first nucleic acid strand binds to a second nucleic acid strand made up of nucleotides that are complementary to those in the first strand, the two strands bind to form a double strand. In various embodiments, "nucleic acid sequencing data," "nucleic acid sequencing information," "nucleic acid sequence," "genomic sequence," "genetic sequence," or "fragment sequence," or "nucleic acid sequencing read," or "nucleic acid sequence read," or "sequence read" denotes any information or data that is indicative of the order of the nucleotide bases (e.g., adenine, guanine, cytosine, and thymine/uracil) in a molecule (e.g., whole genome, whole transcriptome, exome, oligonucleotide, polynucleotide, fragment, etc.) of DNA or RNA.

In various embodiments, a "polynucleotide", "nucleic acid", or "oligonucleotide" refers to a linear polymer of nucleosides (including deoxyribonucleosides, ribonucleosides, or analogs thereof) joined by internucleosidic linkages. Typically, a polynucleotide comprises at least three nucleosides. Usually oligonucleotides range in size from a few monomeric units, e.g. 3-4, to several hundreds of monomeric units. Whenever a polynucleotide such as an oligonucleotide is represented by a sequence of letters, such as "ATGCCTG," it will be understood that the nucleotides are in 5'→3' order from left to right and that "A" denotes deoxyadenosine, "C" denotes deoxycytidine, "G" denotes deoxyguanosine, and "T" denotes thymidine, unless otherwise noted. The letters A, C, G, and T may be used to refer to the bases themselves, to nucleosides, or to nucleotides comprising the bases, as is standard in the art.

The term "locus" as used herein refers to a specific position on a chromosome or a nucleic acid molecule. Alleles of a locus are located at identical sites on homologous chromosomes.

As used herein, the terms "adapter" or "adapter and its complements" and their derivatives, refers to any linear oligonucleotide which can be ligated to a nucleic acid molecule of the disclosure. Optionally, the adapter includes a nucleic acid sequence that is not substantially complementary to the 3' end or the 5' end of at least one target sequences within the sample. In some embodiments, the adapter is substantially non-complementary to the 3' end or the 5' end of any target sequence present in the sample. In some embodiments, the adapter includes any single stranded or double-stranded linear oligonucleotide that is not substantially complementary to an amplified target sequence. In some embodiments, the adapter is substantially non-complementary to at least one, some or all of the nucleic acid molecules of the sample. In some embodiments, suitable adapter lengths are in the range of about 10-100 nucleotides, about 12-60 nucleotides and about 15-50 nucleotides in length. An adapter can include any combination of nucleotides and/or nucleic acids. In some aspects, the adapter can include one or more cleavable groups at one or more locations. In another aspect, the adapter can include a sequence that is substantially identical, or substantially complementary, to at least a portion of a primer, for example a universal primer. In some embodiments, the adapter can include a barcode or tag to assist with downstream cataloguing, identification or sequencing. In some embodiments, a single-stranded adapter can act as a substrate for amplification when ligated to an amplified target sequence, particularly in the presence of a polymerase and dNTPs under suitable temperature and pH.

As used herein, "DNA barcode" or "DNA tagging sequence" and its derivatives, refers to a unique short (e.g., 6-14 nucleotide) nucleic acid sequence within an adapter that can act as a 'key' to distinguish or separate a plurality of amplified target sequences in a sample. For the purposes of this disclosure, a DNA barcode or DNA tagging sequence can be incorporated into the nucleotide sequence of an adapter.

In some embodiments, the disclosure provides for amplification of multiple target-specific sequences from a population of target nucleic acid molecules. In some embodiments, the method comprises hybridizing one or more target-specific primer pairs to the target sequence, extending a first primer of the primer pair, denaturing the extended first primer product from the population of nucleic acid molecules, hybridizing to the extended first primer product the second primer of the primer pair, extending the second primer to form a double stranded product, and digesting the target-specific primer pair away from the double stranded product to generate a plurality of amplified target sequences.

In some embodiments, the digesting includes partial digesting of one or more of the target-specific primers from the amplified target sequence. In some embodiments, the amplified target sequences can be ligated to one or more adapters. In some embodiments, adapters can include one or more DNA barcodes or tagging sequences. In some embodiments, amplified target sequences once ligated to an adapter can undergo a nick translation reaction and/or further amplification to generate a library of adapter-ligated amplified target sequences.

In some embodiments, the methods of the disclosure include selectively amplifying target sequences in a sample containing a plurality of nucleic acid molecules and ligating the amplified target sequences to at least one adapter and/or barcode. Adapters and barcodes for use in molecular biology library preparation techniques are well known to those of skill in the art. The definitions of adapters and barcodes as used herein are consistent with the terms used in the art. For example, the use of barcodes allows for the detection and analysis of multiple samples, sources, tissues or populations of nucleic acid molecules per multiplex reaction. A barcoded and amplified target sequence contains a unique nucleic acid sequence, typically a short 6-15 nucleotide sequence, that identifies and distinguishes one amplified nucleic acid molecule from another amplified nucleic acid molecule, even when both nucleic acid molecules minus the barcode contain the same nucleic acid sequence. The use of adapters allows for the amplification of each amplified nucleic acid molecule in a uniformed manner and helps reduce strand bias. Adapters can include universal adapters or propriety adapters both of which can be used downstream to perform one or more distinct functions. For example, amplified target sequences prepared by the methods disclosed herein can be ligated to an adapter that may be used downstream as a platform for clonal amplification. The adapter can function as a template strand for subsequent amplification using a second set of primers and therefore allows universal amplification of the adapter-ligated amplified target sequence. In some embodiments, selective amplification of target nucleic acids to generate a pool of amplicons can further comprise ligating one or more barcodes and/or adapters to an amplified target sequence. The ability to incorporate barcodes enhances sample throughput and allows for analysis of multiple samples or sources of material concurrently.

In this application, "reaction confinement region" generally refers to any region in which a reaction may be confined and includes, for example, a "reaction chamber," a "well," and a "microwell" (each of which may be used interchangeably). A reaction confinement region may include a region in which a physical or chemical attribute of a solid substrate can permit the localization of a reaction of interest, and a discrete region of a surface of a substrate that can specifically bind an analyte of interest (such as a discrete region with oligonucleotides or antibodies covalently linked to such surface), for example. Reaction confinement regions may be hollow or have well-defined shapes and volumes, which may be manufactured into a substrate. These latter types of reaction confinement regions are referred to herein as microwells or reaction chambers, and may be fabricated using any suitable microfabrication techniques. Reaction confinement regions may also be substantially flat areas on a substrate without wells, for example.

A plurality of defined spaces or reaction confinement regions may be arranged in an array, and each defined space or reaction confinement regions may be in electrical communication with at least one sensor to allow detection or measurement of one or more detectable or measurable parameter or characteristics. This array is referred to herein as a sensor array. The sensors may convert changes in the presence, concentration, or amounts of reaction by-products (or changes in ionic character of reactants) into an output signal, which may be registered electronically, for example, as a change in a voltage level or a current level which, in turn, may be processed to extract information about a chemical reaction or desired association event, for example, a nucleotide incorporation event. The sensors may include at least one chemically sensitive field effect transistor ("chemFET") that can be configured to generate at least one output signal related to a property of a chemical reaction or target analyte of interest in proximity thereof. Such properties can include a concentration (or a change in concentration) of a reactant, product or by-product, or a value of a physical property (or a change in such value), such as an ion concentration. An initial measurement or interrogation of a pH for a defined space or reaction confinement regions, for example, may be represented as an electrical signal or a voltage, which may be digitalized (e.g., converted to a digital representation of the electrical signal or the voltage). Any of these measurements and representations may be considered raw data or a raw signal.

In various embodiments, the phrase "base space" refers to a representation of the sequence of nucleotides. The phrase "flow space" refers to a representation of the incorporation event or non-incorporation event for a particular nucleotide flow. For example, flow space can be a series of values representing a nucleotide incorporation event (such as a one, "1") or a non-incorporation event (such as a zero, "0") for that particular nucleotide flow. Nucleotide flows having a non-incorporation event can be referred to as empty flows, and nucleotide flows having a nucleotide incorporation event can be referred to as positive flows. It should be understood that zeros and ones are convenient representations of a non-incorporation event and a nucleotide incorporation event; however, any other symbol or designation could be used alternatively to represent and/or identify these events and non-events. In particular, when multiple nucleotides are incorporated at a given position, such as for a homopolymer stretch, the value can be proportional to the number of nucleotide incorporation events and thus the length of the homopolymer stretch.

FIG. 1 illustrates an example of a primer design for detection of a fusion, where the 5' primer and 3' primer each have a molecular tag. For detecting intergenic fusions, primers are designed within an amplifiable range of the known breakpoint for each of gene. For example, the 5' primer 104 is designed to be on the left side of the breakpoint 102 on gene A and the 3' primer 106 is designed to be on the right side of the breakpoint 102 on gene B. Each primer is within a number of bases, or range 112 and 114, of the respective breakpoint 102, so that the resulting amplicons include portions of gene A and gene B that are fused at the fusion breakpoint 102. The ranges 112 and 114 are related to the amplicon size. Depending on the amplicon size, the primers may be designed at certain ranges 112 and 114 from the breakpoint 102. In some embodiments, the fusion design ranges 112 and 114 may indicate a maximal amount of sequence that can be used for primer design. Primers 104 and 106 targeting a specific fusion breakpoint 102 flank the breakpoint 102 to generate fusion amplicons. The fusion ID amplicon in FIG. 1 represents an ideal fusion amplicon that can identify the presence of the targeted fusion. The same strategy may be applied for assays designed to detect intragenic fusions events. For example, in FIG. 1, gene A would be exon A and gene B would be exon B. Intragenic events may include events such as exon-skipping, non-canonical and wild type transcripts. For identifying individual polynucleotide molecules, molecular tags 108 and 110 are appended to the 5' primer 104 and the 3' primer 106, respectively, including a prefix tag 108 appended to the 5' primer 104 and a suffix tag 110 appended to the 3' primer 106. Individual polynucleotide molecules are labeled with unique molecular tags, amplified in a PCR reaction and sequenced generating fusion amplicons. The fusion amplicons for a given targeted fusion may include the sequence for fusion ID amplicon and the prefix tag 108 for the 5' end and the suffix tag 110 for the 3'end. PCR amplification and sequencing may produce multiple fusion amplicons resulting in multiple sequence reads per original tagged polynucleotide molecule when the targeted fusion is present. The unique molecular tag is used to identify the sequence reads that originate from the same polynucleotide molecule and classify them into families having the same tag sequence.

A family, or molecular family, refers the set of sequence reads having the same unique molecular tags. The family size is the number of sequence reads in the family. A functional family is a family that has a number of members that is greater than a minimum family size. The minimum family size can be any integer value. For example, the minimum family size can be three or greater.

Figure 2:
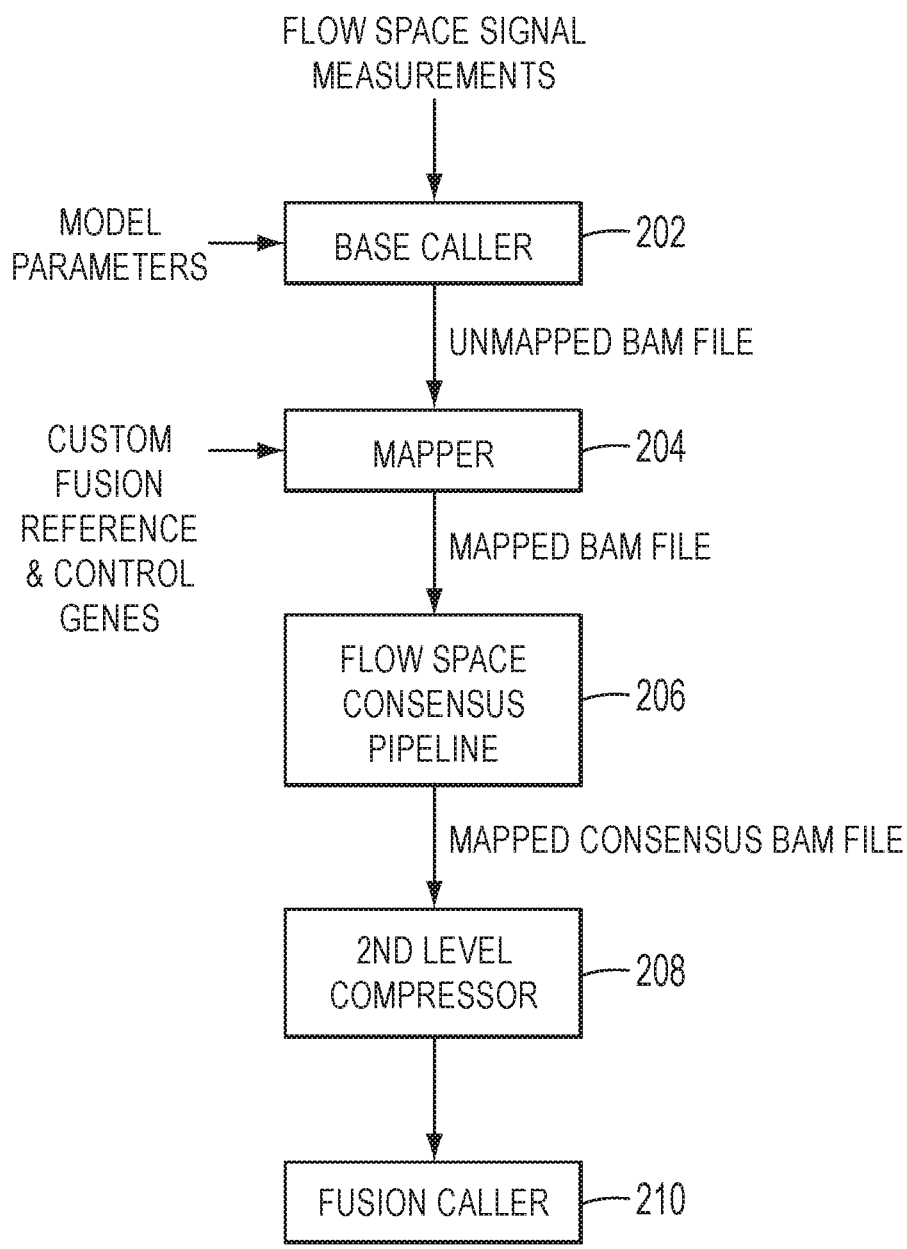
FIG. 2 is a block diagram of an exemplary method for generating consensus compressed data for detecting fusions, in accordance with an embodiment.

FIG. 2 is a block diagram of an exemplary method for generating consensus compressed data for detecting fusions, in accordance with an embodiment. Flow space signal measurements may be provided to a processor by a nucleic acid sequencing device. In some embodiments, each flow space signal measurement represents a signal amplitude or intensity measured in response to an incorporation or non-incorporation of a flowed nucleotide by sample nucleic acids in microwells of a sensor array. For an incorporation event, the signal amplitudes depend on the number of bases incorporated at one flow. For homopolymers, the signal amplitudes increase with increasing homopolymer length. The processor may apply a base caller 202 to generate base calls for a sequence read by analyzing flow space signal measurements.

Figure 4:
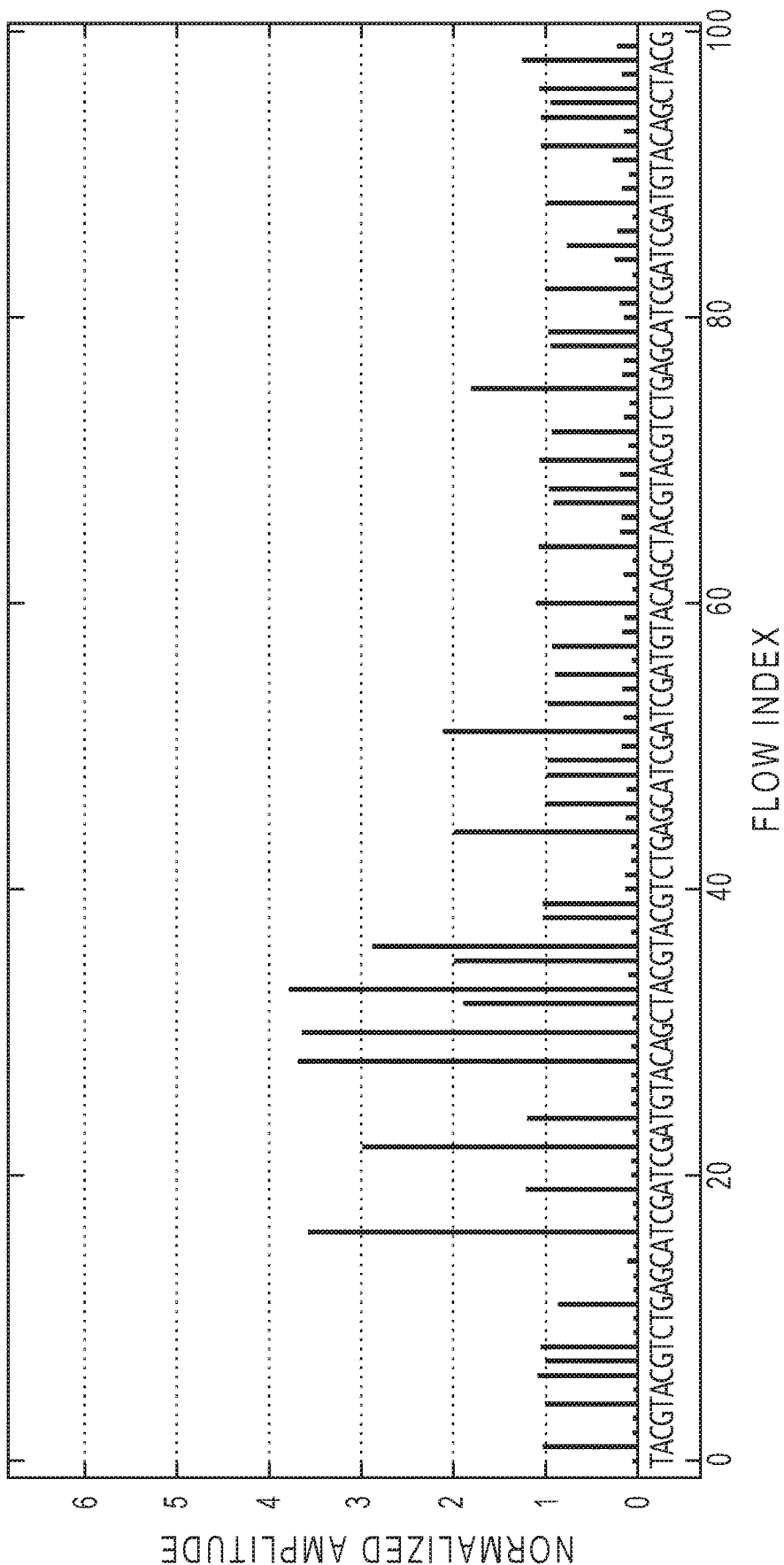
FIG. 4 shows an exemplary representation of flow space signal measurements from which base calls may be made.

FIG. 4 shows an exemplary representation of flow space signal measurements from which base calls may be made. In this example, the x-axis shows the flow index and the nucleotide that was flowed in a flow sequence. The bars in the graph show the amplitudes of the flow space signal measurements for each flow from a particular location of a microwell in the sensor array. The flow space signal measurements may be raw acquisition data or data having been processed, such as, e.g., by scaling, background filtering, normalization, correction for signal decay, and/or correction for phase errors or effects, etc. The base calls may be made by analyzing any suitable signal characteristics (e.g., signal amplitude or intensity). The structure and/or design of a sensor array, signal processing and base calling for use with the present teachings may include one or more features described in U.S. Pat. Appl. Publ. No. 2013/0090860, Apr. 11, 2013, incorporated by reference herein in its entirety.

Once the base sequence for the sequence read is determined, the sequence reads may be provided to mapper 204, for example, in an unmapped BAM file. In some embodiments, the mapper 204 aligns the sequence reads to a custom fusion reference sequence and control genes reference sequences to determine aligned sequence reads and associated mapping quality parameters. The custom fusion reference may comprise a chimeric sequence for a targeted fusion. The control gene reference sequences may include RNA transcript sequences for housekeeping genes. Housekeeping genes are required for the maintenance of basic cellular function and are expressed in cells of an organism in normal and pathological conditions. The targeted fusion reference sequence and control gene reference sequence may be provided in a file using the FASTA file format or other suitable file format. Methods for aligning sequence reads for use with the present teachings may include one or more features described in U.S. Pat. Appl. Publ. No. 2012/0197623, published Aug. 2, 2012, incorporated by reference herein in its entirety. The aligned sequence reads may be provided to the flow space consensus pipeline 206, for example, in a mapped BAM file.

The BAM file format structure is described in "Sequence Alignment/Map Format Specification," Sep. 12, 2014 (www.github.com/samtools/hts-specs), referred to as "BAM specification" herein. As described herein, a "BAM file" refers to a file compatible with the BAM format. As described herein, an "unmapped" BAM file refers to a BAM file that does not contain aligned sequence read information or mapping quality parameters and a "mapped" BAM file refers to a BAM file that contains aligned sequence read information and mapping quality parameters. As described herein, a "consensus" BAM file refers to a BAM file that contains consensus compressed data.

In some embodiments, a read structure for a sequence read with molecular tagging may include, starting from the 5' end, a library key, a barcode sequence, a barcode adapter, a prefix molecular tag, a sequence template, a suffix molecular tag, and a P1 adapter. Base calling may include trimming the library key, barcode sequence and barcode adapter from the rest of the sequence read and storing them in the key sequence (KS) tag field of the read group header @RG of the BAM file format. Base calling may include trimming the P1 adapter from the sequence read and storing it in a comment line @CO of the BAM header.

In some embodiments, the base caller 202 may be configured to detect the tag structure and trim the tag from the sequence read. Trimmed tags may be stored in the BAM read group header (@RG) in fields for custom tags ZT (for a prefix tag, for example) and YT (for a suffix tag, for example). Since the read group header is associated with the sequence read data of the template, the integrity of the tag's association with the family group may be maintained. Subsequent mapping or alignment with a reference sequence may be applied to the template sequence without a prefix tag or a suffix tag. This reduces the possibility of erroneous mapping of a portion of a tag to the reference sequence.

In some embodiments, a tag sequence may include a subset of random bases and a subset of known bases. A tag trimming method may require that the sequence of bases in the tag portion of the sequence read match the known bases. A tag trimming method may select a base string that has a number of bases equal to the known length of a tag. In some embodiments, a tag trimming method may detect and correct sequencing error in the tag, such as insertions and deletions. Correcting sequencing errors in the tag may provide more accurate family identification.

In some embodiments, the mapped BAM file may store a plurality of sequence reads, a plurality of vectors of flow space signal measurements and a plurality of sequence alignments corresponding to the sequence reads. The mapped BAM file may store the vectors of flow space signal measurements in the custom tag field ZM. The mapped BAM file may store the model parameters in the custom tag field ZP. The mapped BAM file may store the molecular tag sequences associated with the sequence reads in the BAM read group header, as described above. The mapped BAM file may be stored in memory and provided to the flow space consensus pipeline 206. In some embodiments, other file formats may be used to store a plurality of sequence reads, a plurality of vectors of flow space signal measurements, a plurality of sequence alignments and molecular tag sequences corresponding to the sequence reads.

Figure 3:
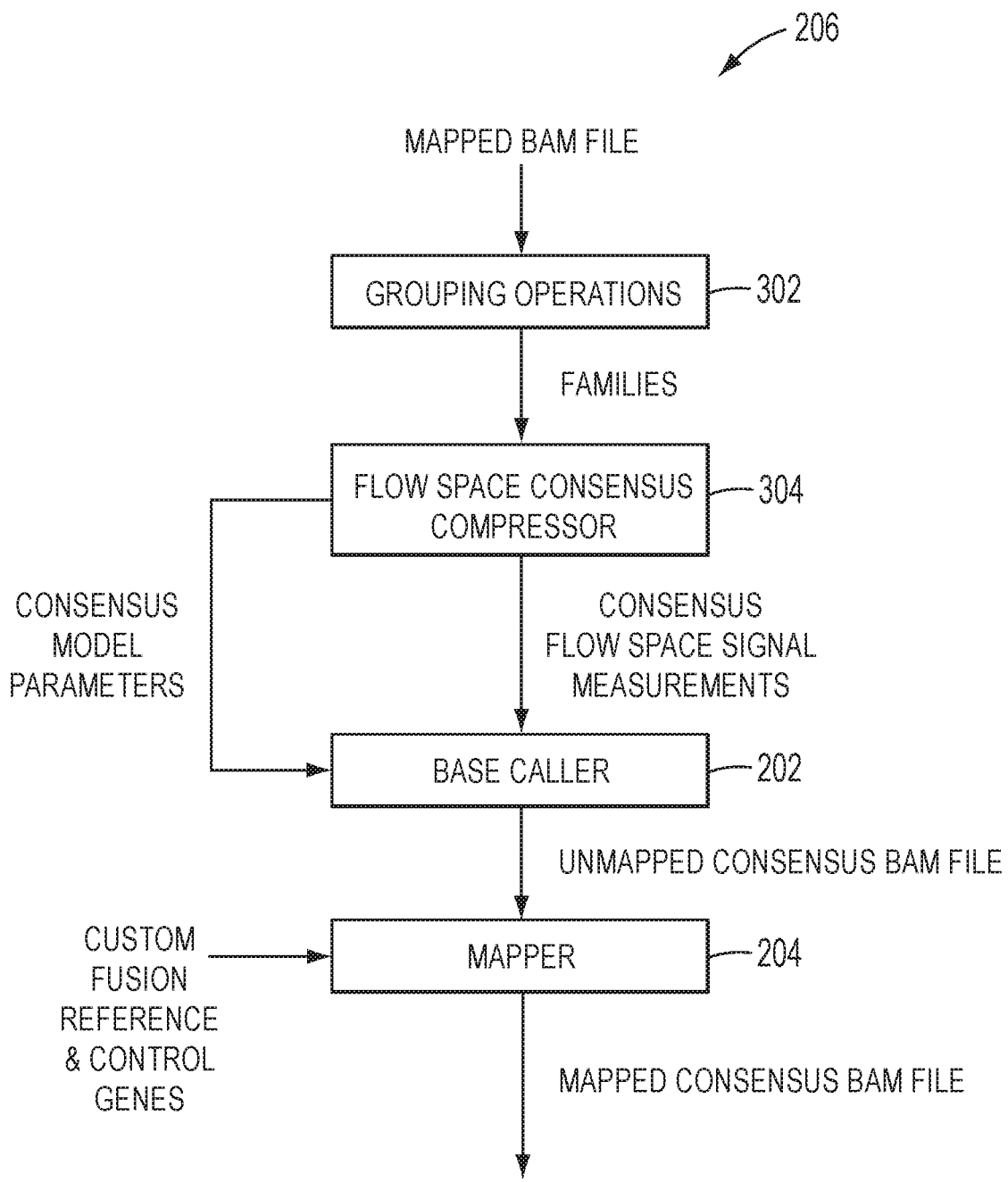
FIG. 3 is a block diagram of an exemplary method for the flow space consensus pipeline, in accordance with an embodiment.

FIG. 3 is a block diagram of an exemplary method for the flow space consensus pipeline 206, in accordance with an embodiment. Grouping operations 302 may use the molecular tag sequence information to identify families of sequence reads and corresponding flow space signal measurements. Grouping operations 302 may compare molecular tag sequences associated with the sequence reads and apply a grouping threshold. For example, the criterion of the grouping threshold can require that all tag sequences of members of a group of sequence reads have 100% tag sequence identity. Sequence reads and corresponding flow space signal measurements that are determined to share a common tag sequence, by meeting the criterion of the grouping threshold, are grouped into a given family, where the common tag sequence is unique to that family. Each family will have a number of members which is the number of sequence reads grouped in the family. In some embodiments, families not having at least a minimum number of members will not be further processed and may be removed from memory. Methods for grouping sequence reads based on molecular tag sequences for use with the present teachings may include one or more features described in U.S. Pat. Appl. Publ. No. 2016/0362748, published Dec. 15, 2016, incorporated by reference herein in its entirety.

In some embodiments, the flow space consensus compressor 304 may determine consensus compressed data based on the flow space signal measurements for each of the grouped families as follows:

A. Calculate an arithmetic mean of the vectors of flow space signal measurements of each grouped family to form a vector of consensus flow space signal measurements for each family.

B. Calculate a standard deviation of the vectors of flow space signal measurements of each family to form a vector of standard deviations for each family.

In some embodiments, the flow space consensus compressor 304 may receive at least one model parameter corresponding to each vector of flow space signal measurements. The flow space consensus compressor 304 may calculate an arithmetic mean of model parameters of the family to form at least one consensus model parameter for the family. The model parameters may be used for base calling, as described below. In some embodiments, the model parameters may include an incomplete extension (IE) parameter and a carry forward (CF) parameter for each vector of flow space signal measurements. The flow space consensus compressor 304 may calculate an arithmetic mean of the IE parameters and an arithmetic mean of the CF parameters of each family to form a consensus IE parameter and a consensus CF parameter for each family.

In some embodiments, the base caller 202 may be applied to the vector of consensus flow space signal measurements for each family to generate a consensus base sequence for the respective family. A consensus base sequence is also referred to herein as a consensus sequence read. The consensus model parameters may be used in applying a model for base calling. For example, a consensus incomplete extension (IE) parameter and a consensus carry forward (CF) parameter for each family may be provided to the base caller 202. The base calling may include one or more features described in U.S. Pat. Appl. Publ. No. 2013/0090860, published Apr. 11, 2013, and/or U.S. Pat. Appl. Publ. No. 2012/0109598, published May 3, 2012, which are all incorporated by reference herein in their entirety. A consensus sequence alignment for the consensus base sequence may be determined by comparing the consensus base sequence to the sequence read in the family having the highest mapping quality. If the consensus base sequence matches the sequence read having the highest mapping quality, the corresponding sequence alignment is selected as the consensus sequence alignment. If the consensus base sequence does not match the sequence read in the family having the highest mapping quality, the mapper 204 may align the consensus base sequence to the targeted fusion reference sequence and control genes reference sequences to determine the consensus sequence alignment. Methods for aligning consensus sequence reads may include one or more features described in U.S. Pat. Appl. Publ. No. 2012/0197623, published Aug. 2, 2012, incorporated by reference herein in its entirety. In some embodiments, about 1% of consensus sequence reads, on average, may need realignment by the mapper 204.

In some embodiments, the processor may store the consensus compressed data for each family in a compressed data structure in a memory. The consensus compressed data may include the consensus sequence read, the consensus sequence alignment, the vector of consensus flow space signal measurements, the vector of standard deviations and the number of members for each family. The consensus compressed data may further include a set of consensus model parameters for each family. If the family has been separated into subfamilies, the consensus compressed data may further include the consensus sequence read, the consensus sequence alignment, the vector of consensus flow space signal measurements, the vector of standard deviations and the number of members for each subfamily. In some embodiments, the compressed data structure may be compatible with the BAM file format to produce a mapped consensus BAM file. The BAM specification allows the user to define custom tag fields. For example, custom tag fields may be defined for the BAM file used to store some of the consensus compressed data, as shown in Table 1.

TABLE 1

| BAM Custom Tag Field | DATA |
| --- | --- |
| ZM | Consensus flow space signal measurements |
| ZP | Consensus model parameters |
| ZS | Standard deviations of flow space signal measurements |
| ZR | Number of sequence reads, or members, in family or subfamily |

The original sequence reads, original vectors of flow space signal measurements and original model parameters for each family are not included in the consensus compressed data and may be removed from memory. In some embodiments, the compressed data structure may use a different format protocol than the BAM file format, including custom file formats.

Figure 5:
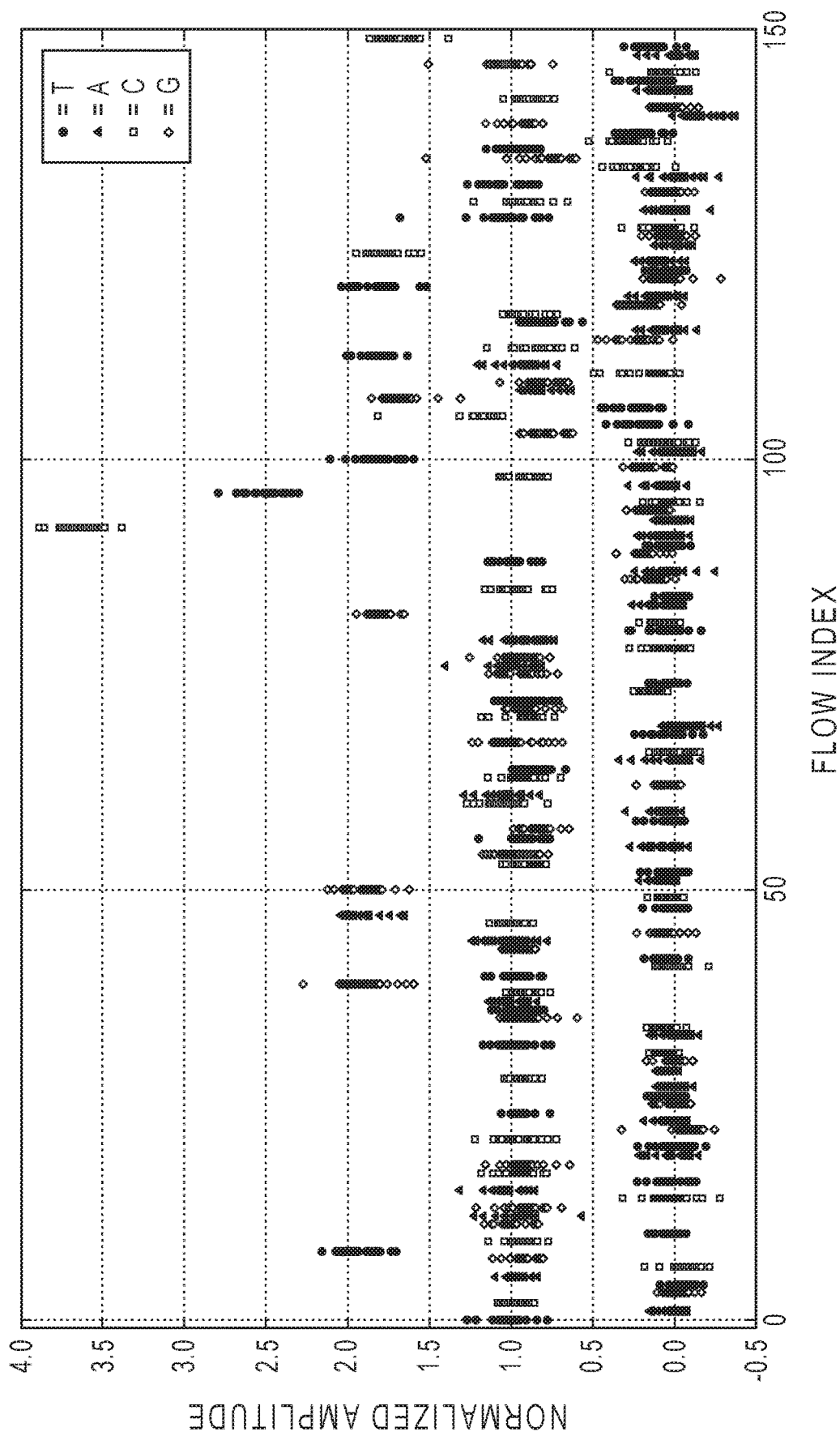
FIG. 5 illustrates an exemplary plot of flow space signal measurements for a single family.

FIG. 5 illustrates an exemplary plot of flow space signal measurements for a single family. The flow index indicates the j-th flow in the flow sequence. The normalized amplitude indicates the value of the flow space signal measurement. The type of plot symbol corresponds to the nucleotide at the particular flow. This plot of flow space signal measurements corresponds to a single family of sequence reads associated with a common molecular tag. The values of the flow space signal measurements at each flow are clustered near similar values. The flow index corresponds to the element index in the vector of flow space signal measurements. The flow space signal measurements represented in this plot may be input to the flow space consensus compressor 304.

Figure 6:
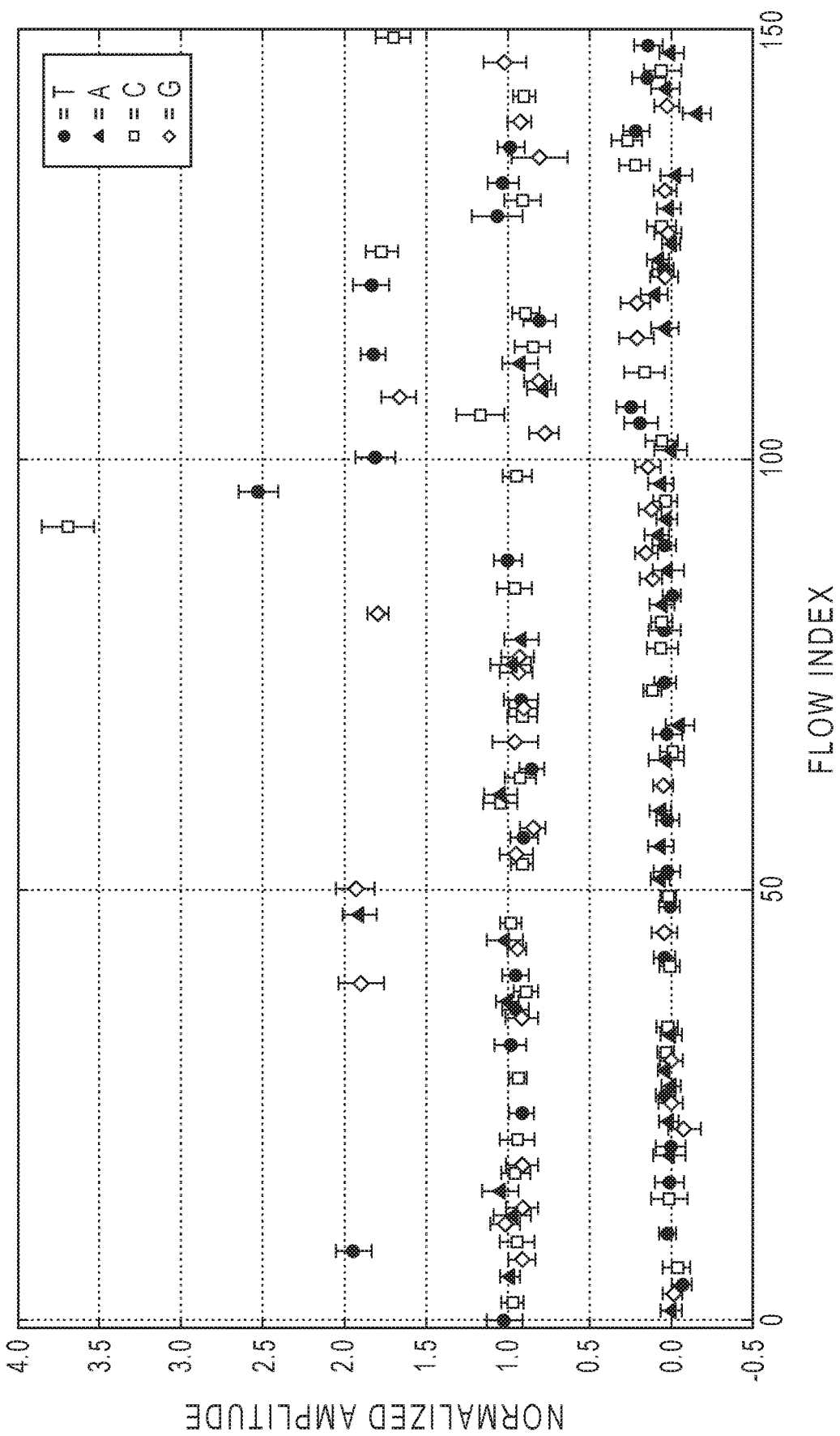
FIG. 6 illustrates an exemplary plot of consensus flow space signal measurements for a single family.

FIG. 6 illustrates an exemplary plot of consensus flow space signal measurements for a single family. This plot shows consensus flow space signal measurement values resulting from consensus calculations on the flow space signal measurements shown in FIG. 5. The plot symbols indicate the arithmetic means that are elements of the vector of consensus flow space measurements for the family. The bars indicate the standard deviations that are elements of the vector of standard deviations for the family.

For bidirectional sequencing, a first family may be designated for forward sequence reads and a second family may be designated for reverse sequence reads. The prefix and suffix tags of the forward read may be the reverse complement of the prefix and suffix tags for the reverse read, as shown in the example of Table 2.

TABLE 2

| Read Direction | Prefix Tag | Suffix Tag | Tag | Number of Sequence Reads |
|---|---|---|---|---|
| Forward Read | ACT | GGT | ACTGGT | 10 |
| Reverse Read | ACC | AGT | ACCAGT | 10 |
| Reverse Complement of Reverse Read Tags | GGT | ACT | ACTGGT | 20 |

In some embodiments, a family may be split into subfamilies, resulting in more than one consensus sequence read per family having the same molecular tags. Subfamilies may be formed for flow synchronization so that each subfamily has synchronized flow space signal measurements for determining the vector of consensus flow space measurements. A family may be split into subfamilies when there are variations in sequence reads within the family so that a consensus sequence read is generated for each subfamily. Methods for flow space consensus compression for molecular tagged nucleic acid sequence data for use with the present teachings may include one or more features described in U.S. patent application Ser. No. 15/979,804, filed May 15, 2018, incorporated by reference herein in its entirety.

Returning to FIG. 2, in some embodiments, a second level compressor 208 may be applied to the consensus compressed data prior to fusions analysis. The second level compressor 208 may combine the subfamilies having the same molecular tags into a single family that includes one consensus sequence read. In some embodiments for bidirectional sequencing reads, the second level compressor 208 may combine the families for the forward and reverse sequence reads as follows:
1. Determine the reverse complement the prefix and suffix tags of the reverse reads to form a reverse complement tag,
2. Match the reverse complement tag with a forward read tag,
3. Combine the forward read family with the matching tag and the reverse read family into one family including one consensus sequence read.

Referring to Table 2, the number of reads represented by the combined family is the sum of numbers of sequence reads in the forward and reverse read families. The mapped consensus BAM file may be modified to include the combined family information and remove the subfamily information. The sum value may be entered in the ZR field of the mapped consensus BAM file. The second level compressor 208 provides a single consensus sequence read for a combined family. By eliminating one subfamily's consensus sequence read for each combined family, the second level compressor 208 provides additional data compression. After second level compression, the consensus compressed data may be provided to the fusion caller 210.

Figure 7:
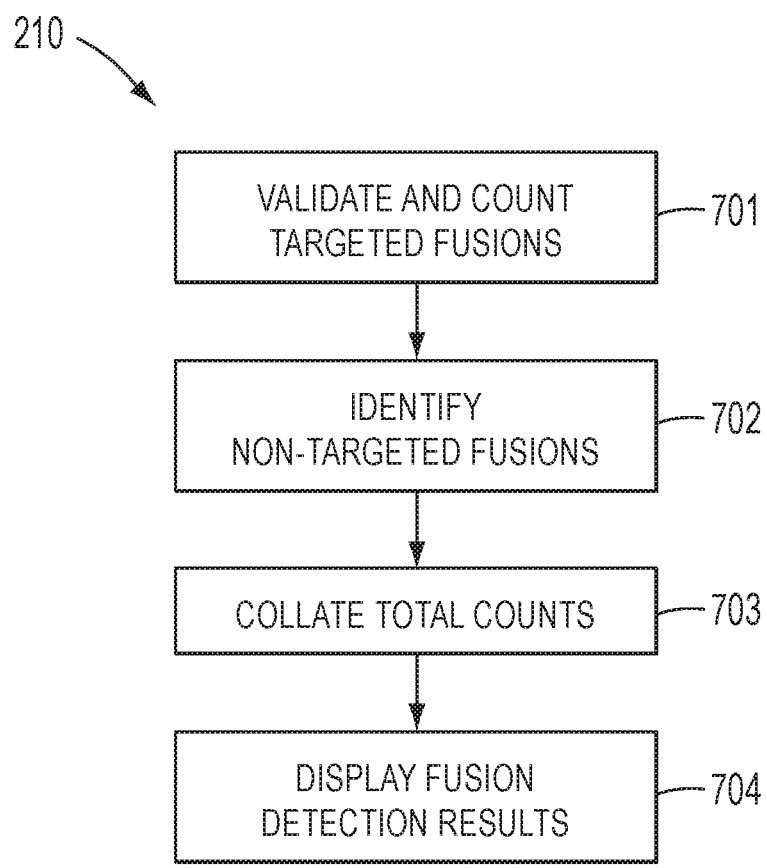
FIG. 7 is a block diagram of an exemplary method of using consensus compressed data for fusion calling operations, in accordance with an embodiment.

FIG. 7 is a block diagram of an exemplary method of using consensus compressed data for fusion calling operations. In some embodiments, at step 701, the processor may validate and provide counts for targeted fusions by the following:
a. Identify the consensus sequence reads that are eligible to be counted for targeted fusion detection by analyzing characteristics of the alignment of the consensus sequence read with the targeted fusion reference sequence.
b. For eligible sequence reads, count the number of families corresponding to the eligible consensus sequence reads that align with each targeted fusion reference sequence to give a family count. For bidirectional sequencing, count the number of families per strand to give a family count per strand.
c. Apply a minimum molecular count threshold to the family count for each targeted fusion. For example, a minimum molecular count threshold can be set at a value greater than or equal to 3. For bidirectional sequencing, apply a minimum molecular count threshold per strand to the family count per strand. For example, the minimum molecular count threshold per strand can be set at a value greater than or equal to 1.
d. Sum the numbers of sequence reads for the families corresponding to the eligible consensus sequence reads that align with each targeted fusion reference sequence to give a read count for each targeted fusion. The number of sequence reads for each family may be included in the mapped consensus BAM file.
e. Apply a minimum read count threshold to the read count for each targeted fusion. For example, a minimum read count threshold can be set at a value greater than or equal to 21.
f. Determine sample quality control (QC) parameters related to the process controls. The process controls, or expression controls, indicate the results of alignments of consensus sequence reads with the control gene reference sequences as determined by the mapper 204 and included in the mapped consensus BAM file. In some embodiments, sample QC parameters may include a minimum number of process controls required for validation. For example, where 2 control genes are used, setting the minimum number of process controls to 1, means that consensus sequence reads aligned to the control gene reference sequences should be present for at least 1 of the 2 control genes. For example, for bidirectional sequencing where 6 control genes are used, setting the minimum number of process controls to 3 means that consensus sequence reads aligned to the control gene reference sequences should be present for at least 3 of the 6 control genes. A process control target may be called as Present if, for consensus sequence reads aligned to the control gene reference sequence, the family count is greater than the minimum molecular count threshold and the read count is greater than or equal to the read count threshold. In some embodiments, sample QC parameters may include minimum total of mapped sequence reads for the fusion panel. For example, the minimum total of mapped sequence reads may have a value of 20,000. In some embodiments, sample QC parameters may include a minimum average sequence read length for all the sequence reads in the sample. For example, the minimum average read length may have a value of 50.

g. Determine a call or a no-call decision on the presence of the targeted fusion. If the minimum molecular count threshold, the minimum read count threshold and the sample QC parameters are met for the targeted fusion breakpoint, a call decision that the targeted fusion is present may be made. If one or more of the minimum molecular count threshold and the minimum read count threshold are not met for the targeted fusion breakpoint, a not-present decision may be made. In some embodiments, if a sample has fewer than the minimum total mapped sequence reads, all the targeted fusions in the panel are given a no-call decision. In some embodiments, if the average sequence read length from all the sequences is calculated and if the average is less than minimum average sequence read length, all the targeted fusions in the panel are given a no-call decision. In some embodiments, if the number of process controls detected is less than the minimum number of process controls threshold, all the targeted fusions in the panel are given a no-call decision.

In some embodiments, the step to identify eligible consensus sequence reads (step a, above) includes analyzing the consensus sequence reads to ensure that each aligned consensus sequence read has representation from both gene partners involved in the gene fusion before it is counted for fusion detection. Characteristics of the alignment of the consensus sequence read with the targeted fusion reference sequence may include a homology characteristic, a mapping quality characteristic and breakpoint scanning characteristic. The processor analyzes each aligned consensus sequence read for these characteristics as follows:

i. Determine whether the consensus sequence read spans the fusion breakpoint on the targeted fusion reference sequence.
 ii. Determine the homology level of the consensus sequence read with each partner sequence, to give first and second homology levels. Homology is the number of bases in the overlap between the consensus sequence read and the target sequence. A partner sequence is that portion of targeted fusion reference sequence that is on one side of the fusion breakpoint. Each targeted fusion has first and second partner sequences, one on each side of the breakpoint in the targeted fusion reference sequence.
 iii. Compare the first and second homology levels to a minimum homology threshold. The minimum homology threshold may be selected base on a desired sensitivity and stringency. For example, a minimum homology threshold may be set at 60% for high sensitivity/low stringency, 70% for a default value, and 80% for high stringency. Other values for the minimum homology threshold may also be used. These values may range from 50% to 100%.
 iv. Determine a mapping quality value for the aligned consensus sequence read within each partner sequence to produce first and second mapping quality values. The mapping quality value may be determined by calculating a ratio of the number of matching bases in the aligned consensus sequence read that match the partner sequence to the number of overlapping bases in the aligned consensus sequence read that overlap the partner sequence.
 v. Compare the first and second mapping quality values to a mapping quality threshold. For example, the mapping quality threshold may have a value of 66.6%. Other mapping quality threshold values may also be used. These values may range from 50% to 100%.
 vi. When the consensus sequence read meets the criteria of spanning the fusion breakpoint, having first and second homology levels that are at least the minimum homology threshold and having first and second mapping quality values that are at least the mapping quality threshold, it is an eligible consensus sequence read for step b, above. In some embodiments, when the consensus sequence read does not meet these criteria it may be provided to step 702 in FIG. 7 to identify the presence of a non-targeted fusion or it may be filtered away.

In some embodiments, the consensus sequence reads that do not meet the above criteria may partially map to the targeted fusion reference sequences. The partially mapped consensus sequence reads can have a mapped portion and an unmapped portion. The mapped portion may be near the beginning of the consensus sequence read with the unmapped portion near the end of the consensus sequence read, or the unmapped portion can be near the beginning of the consensus sequence read and the mapped portion can be near the end of the consensus sequence read.

In some embodiments, at step 702, the processor analyzes the partially mapped consensus sequence reads to identify any evidence of non-targeted fusion combinations as follows:

a) Split the partially mapped consensus sequence read into a mapped portion and an unmapped portion, such that a partially mapped consensus sequence read generates two read fragments.
 b) Align the read fragments independently to the fusion reference sequences. For example, a first fragment of a partially mapped read will map to a first locus within the fusion reference sequences and the second fragment of the partially mapped read will map to a second locus within the fusion reference sequences. A locus may be a mapped location for the read fragment on the reference sequence. For example, the two read fragments may align to two different fusion reference sequences. For example, the two read fragments may align to a same fusion reference sequence.
 c) Determine whether the first fragment aligned with the 5' end and the second fragment aligned with the 3' end of the respective fusion reference sequences.
 d) Determine whether the mapping quality values for the aligned read fragments within each partner sequence are greater than or equal to a mapping quality threshold. Mapping quality values are described in steps iv and v above. For example, the mapping quality threshold may have a value of 66.6%.
 e) Determine homology levels for the first and second aligned read fragments. Homology levels are described in step ii, above. Sum the homology levels to give a combined homology level for both of the read fragments.
 f) Determine whether the combined homology level is greater than or equal to the combined homology threshold. For example, the combined homology threshold may be 150%. For example, the homology levels of 100% for the first fragment and 50% for the second fragment are allowed. For example, the homology levels of 90% for the first fragment and 70% for the second fragment are allowed. For example, the homology levels of 80% for the first fragment and 60% for the second fragment are not sufficient because the sum is less than 150%.

g) For aligned read fragments that meet combined homology level threshold and the mapping quality threshold, count the number of families corresponding to the consensus read sequences that generated the read fragments aligned with the respective fusion reference sequences to give a family count.

h) Apply a minimum molecular count threshold to the family count. For example, a minimum molecular count threshold can be set at a value greater than or equal to 3. For bidirectional sequencing, apply a minimum molecular count threshold per strand to the family count per strand. For example, the minimum molecular count threshold per strand can be set at a value greater than or equal to 1.

i) Sum the numbers of sequence reads for the families corresponding to the consensus sequence reads that generated the read fragments aligned with the respective fusion reference sequences to give a read count.

j) Apply a minimum read count threshold to the read count for each targeted fusion. For example, a minimum read count threshold can be set at a value greater than or equal to 21.

Methods for determining fusions in partially mapped sequence reads for use with the present teachings may include one or more features described in U.S. Pat. Appl. Publ. No. 2016/0362748, published Dec. 15, 2016, incorporated by reference herein in its entirety.

In some embodiments, the family counts generated from steps 701 and 702 may be aggregated to form total family counts. The minimum family count threshold may be applied to the total family counts. In some embodiments, the read counts generated from steps 701 and 702 may be aggregated to form total read counts. The minimum read count threshold may be applied on the total read counts.

The methods described with respect to FIGS. 1, 2, 3 and 7 may be applied to both intergenic fusion events and intragenic fusion events. For intergenic fusion events, the targeted fusion reference sequence comprises a reference sequence for the fusion of two genes at the fusion breakpoint. For intragenic fusion events, the targeted fusion reference sequence comprises a reference sequence for the fusion of two exons at a fusion breakpoint from a same gene.

Intragenic fusions events may be designed to detect exon deletions, non-canonical and wild type transcripts. Examples of exon deletion targets include EGFR-EGFR.E1E8.DelPositive (commonly known as EGFRvIII deletion) and MET-MET.M13M15 (MET exon 14 skipping assay). Intragenic fusion events are referred to as RNAExonVariants. In some embodiments, for every gene that has intragenic fusion targets, at least one wild type target that is designed to amplify the canonical transcript of that gene is added. The custom fusion reference and control genes may include a reference sequence for the wild type target. A portion of the consensus sequence reads may align with the wild type reference sequence. The wild type targets are referred to as wild type RNAExonVariants. Additional annotations may be provided for the wild type targets, for example in a BED file format.

In some embodiments, the analyses of RNAExonVariants to detect exon deletions and alternate transcripts, may include computing and reporting the following metrics:

I. Ratio of intragenic fusion RNAExonVariant $V_i$ to wild type RNAExonVariants:

Ratio=(Read count of $V_i$)/(Mean read count of all wild type RNAExonVariants for the same gene).

The read count of $V_i$ for the intragenic fusion may be determined by adding the numbers of sequence reads for the families corresponding to the portion of consensus sequence reads aligned with the targeted fusion reference sequence. A read count of a wild type RNAExonVariant may be determined by adding the numbers of sequence reads for the families corresponding to the portion of consensus sequence reads aligned with the wild type reference sequence.

II. Normalized count within the same gene for an intragenic fusion RNAExonVariant $V_i$:

Norm count=(Read count of $V_i$)/(Sum of read counts of all RNAExonVariants of the same gene).

The sum of read counts of all RNAExonVariants may be determined by adding the read counts corresponding to the wild type reference sequences and the read counts corresponding to the targeted fusion reference sequences for the same gene. The read counts corresponding to the wild type reference sequences may be determined by adding the numbers of sequence reads for the families corresponding to the portions of consensus sequence reads aligned with the wild type reference sequences for the same gene. The read counts corresponding to the target fusion reference sequences may be determined by adding the read counts for the families corresponding to the consensus sequence reads aligned with the targeted fusion reference sequences for the same gene.

At step 703, the processor may collate and format the total counts resulting from the targeted fusions determined in step 701, non-targeted fusions generated in step 703 and additional metrics for RNAExonVariants may be collated and formatted for storage in a file. At step 704, the processor may generate visualizations of the fusion results, such as summary tables and dynamic heat maps of normalized counts per fusion/control gene, for presentation to the user. An example of results is given in Table 3.

TABLE 3

| Variant (Exons) | Mol. Count | Read Count | Detection | QC Test | Type | Ratio to Wild Type | Norm Count within Gene |
|---|---|---|---|---|---|---|---|
| EML4-ALK.E6aA20.AB374361 | 16 | 202 | Present | Pass | FUSION | | |
| EML4-ALK.E6bA20.AB374362 | 5 | 56 | Present | Pass | FUSION | | |

TABLE 3-continued

| Variant (Exons) | Mol. Count | Read Count | Detection | QC Test | Type | Ratio to Wild Type | Norm Count within Gene |
|---|---|---|---|---|---|---|---|
| SLC34A2-ROS1.S4R32.COSF1197 | 340 | 5011 | Present | Pass | FUSION | | |
| SLC34A2-ROS1.S4R34.COSF1198 | 28 | 464 | Present | Pass | FUSION | | |
| CCDC6-RET.C1R12.COSF1271 | 36 | 569 | Present | Pass | FUSION | | |
| TBP.ENCTRL.E3E4 | 328 | 5724 | Present | Pass | Process Control | | |
| HMBS.ENCTRL.E8E9 | 606 | 9008 | Present | Pass | Process Control | | |
| MET.E6E7.WT | 2830 | 43648 | Present | Pass | RNAExon Variant | 1.152864 | 0.53447 |
| MET.E11E12.WT | 2906 | 32073 | Present | Pass | RNAExon Variant | 0.847136 | 0.392734 |
| MET-MET.M13M15 | 432 | 5945 | Present | Pass | RNAExon Variant | 0.157024 | 0.072797 |

Other information may also be included in the table of results, such as locus information, annotation information, analysis name, sample name and barcode ID.

Table 4 shows the resulting compression achieved by the methods described herein for bidirectional sequence read data.

TABLE 4

| Variant (Exons) | Original Read Count | Consensus Compress | 2nd Compress & Filtering |
|---|---|---|---|
| AFM.E12E13.NM_001133.2 | 95 | 19 | 2 |
| APOB.E7E8.NM_000384.2 | 3157 | 483 | 107 |
| CHMP2A.E4E5.NM_014453.2 | 505656 | 85252 | 15094 |
| FBXW2.E5E6.NM_012164.3 | 583591 | 72010 | 10671 |
| GUSB.E7E8.NM_000181.3 | 500218 | 76878 | 9779 |
| HMBS.E3E4.NM_000190.3 | 108978 | 13847 | 2050 |
| ITGB7.E9E10.NM_000889.1 | 24197 | 3482 | 602 |
| LMNA.E1E2.NM_005572.3 | 1259880 | 268496 | 44624 |
| LRP1.E41E42.NM_002332.2 | 2078078 | 305540 | 42782 |
| MET.E11E12.NM_000245.2 | 138973 | 21579 | 2647 |
| MET.E6E7.NM_000245.2 | 121732 | 17652 | 2618 |
| MRPL13.E1E2.NM_014078.5 | 546165 | 70526 | 9997 |
| MTTP.E12E13.NM_000253.2 | 1291 | 85 | 25 |
| MYC.E1E2.NM_002467.4 | 329437 | 63108 | 8104 |
| PSMB2.E3E4.NM_001199779.1 | 1087559 | 159101 | 20576 |
| PUM1.E3E4.NM_001020658.1 | 825501 | 116543 | 19967 |
| SNRPD3.E1E2.NM_004175.3 | 718619 | 121620 | 13362 |
| TBP.E3E4.NM_001172085.1 | 174953 | 16809 | 3069 |
| TRIM27.E7E8.NM_006510.4 | 140781 | 19916 | 2637 |
| VCP.E7E8.NM_007126.3 | 1744231 | 323054 | 33616 |

Table 5 shows the resulting compression achieved by the methods described herein for unidirectional sequence read data.

TABLE 5

| Variant (Exons) | Original read count | Consensus Compress | 2nd Compress & Filtering |
|---|---|---|---|
| CCDC6-RET.C1R12.COSF1271 | 521 | 144 | 35 |
| CUX1-RET.C10R12 | 156 | 128 | 0 |
| EML4-ALK.E15A20.COSF413.1 | 136 | 102 | 0 |
| EML4-ALK.E18A20.COSF487.1 | 9 | 6 | 0 |
| EML4-ALK.E6A19.COSF1296.2 | 2 | 2 | 0 |
| EML4-ALK.E6aA20.AB374361 | 79 | 16 | 10 |
| EML4-ALK.E6bA20.AB374362 | 84 | 16 | 7 |
| EZR-ROS1.E10R34.COSF1267 | 38 | 31 | 0 |
| GOPC-ROS1.G4R36.COSF1188 | 50 | 39 | 0 |
| GOPC-ROS1.G8R35.COSF1139 | 1363 | 1130 | 0 |
| HIP1-ALK.H28A20.1 | 20 | 17 | 0 |
| HMBS.ENCTRL.E8E9 | 5085 | 710 | 482 |
| KIF5B-ALK.K17A20.COSF1257 | 157 | 134 | 0 |
| KIF5B-RET.K16R12.COSF1230 | 1947 | 1505 | 2 |
| KIF5B-RET.K22R12.COSF1253 | 123 | 96 | 0 |
| KIF5B-RET.K24R8.COSF1236 | 1 | 1 | 0 |
| KLC1-ALK.K9A20.COSF1276 | 4 | 3 | 0 |
| LRIG3-ROS1.L16R35.COSF1269.1 | 47 | 35 | 0 |
| MET-MET.M13M15 | 5209 | 2058 | 429 |
| MET.E11E12.WT | 19028 | 3639 | 2255 |
| MET.E6E7.WT | 17573 | 2934 | 1676 |
| SLC34A2-ROS1.S4R32.COSF1196 | 4357 | 965 | 561 |
| SLC34A2-ROS1.S4R34.COSF1198 | 474 | 88 | 42 |
| TBP.ENCTRL.E3E4 | 3762 | 644 | 340 |
| TPR-ALK.T15A20 | 1 | 1 | 0 |

In Tables 4 and 5, the Original Read Count gives the original number of sequence reads that aligned to the loci shown in the Variant (Exons) column. The Consensus Compress column gives the number of aligned consensus sequence reads, or number of families, after compression by the flow space consensus pipeline 206. The much more numerous original sequence reads are replaced by the consensus sequence reads of the consensus compressed data. As a result, significant reduction in data volume is achieved. The 2$^{nd}$ Compress & Filtering column shows the number of aligned consensus sequence reads, or number of families, remaining after applying the second level compressor 208 and filtering out those with consensus sequence reads that are not eligible to be counted for fusion detection. The further decrease in the number of consensus sequence reads results in further reduction in data volume. The overall compression results in significant reductions in the amount of data from the original sequence read data. The compression rates directly relate to the reduction in the amount of memory required to store the consensus sequence read data from the amount of memory required to store the original sequence read data.

In some embodiments, the methods described herein may be performed or implemented at least partly using a distributed, clustered, remote, or cloud computing resource. Compression of the sequence read data to provide consensus compressed data provides advantages for transmitting the data to processors in a distributed, clustered, remote, or cloud computing resource. Since the volume of data is reduced, the bandwidth and/or time required for transmission across the data transfer interfaces between computing resources is reduced. For example, the mapped consensus BAM file may be transferred from a local computing resource to a cloud computing resource for fusion detection operations. The size of the mapped consensus BAM file would be significantly smaller than that of the original mapped BAM file. The smaller size of the mapped consensus BAM file would reduce the bandwidth and/or time required for transmission across a data transfer interface to the cloud computing resource.

According to an exemplary embodiment, there is provided a method for compressing molecular tagged nucleic acid sequence data for fusion detection, comprising (a) receiving a plurality of nucleic acid sequence reads and a plurality of sequence alignments for a plurality of families of sequence reads, wherein each sequence read is associated with a molecular tag sequence, the molecular tag sequence identifying a family of sequence reads resulting from a particular polynucleotide molecule in a nucleic acid sample, each family having a number of sequence reads, wherein a portion of the sequence alignments correspond to sequence reads mapped to a targeted fusion reference sequence; (b) determining a consensus sequence read for each family of sequence reads based on flow space signal measurements corresponding to the sequence reads for the family; (c) determining a consensus sequence alignment for each family of sequence reads, wherein a portion of the consensus sequence alignments correspond to the consensus sequence reads aligned with the targeted fusion reference sequence; (d) generating a compressed data structure comprising consensus compressed data, the consensus compressed data including the consensus sequence read and the consensus sequence alignment for each family; and (e) detecting a fusion using the consensus sequence reads and the consensus sequence alignments from the compressed data structure. The method may further comprise, for bidirectional sequencing wherein a forward consensus sequence read and a reverse consensus sequence read are in separate families, where a forward family is associated with a first prefix tag and a first suffix tag and a reverse family is associated with a second prefix tag and a second suffix tag, combining the forward and reverse families when a reverse complement of the second prefix tag and second suffix tag matches the first prefix tag and the first suffix tag to form a combined family having one consensus sequence read for the compressed data structure. The step of detecting a fusion may further comprise identifying an eligible consensus sequence read based on characteristics of the consensus sequence alignment of the consensus sequence read with the targeted fusion reference sequence. The characteristics may include a homology characteristic, a mapping quality characteristic and a breakpoint spanning characteristic. The step of identifying an eligible consensus sequence read may further comprise determining whether the consensus sequence read aligned with the targeted fusion reference sequence spans a fusion breakpoint of the targeted fusion reference sequence. The step of identifying an eligible consensus sequence read may further comprise determining whether first and second homology levels of the consensus sequence read with first and second partner sequences, respectively, of the targeted fusion reference sequence are greater than or equal to a minimum homology threshold. The step of identifying an eligible consensus sequence read may further comprise determining whether first and second mapping quality values for the consensus sequence read within first and second partner sequences, respectively, of the targeted fusion reference sequence are greater than or equal to a mapping quality threshold. The step of identifying an eligible consensus sequence read may further comprise determining the mapping quality value by calculating a ratio of a number of matching bases in the consensus sequence read that match the partner sequence to a number of overlapping bases in the consensus sequence read that overlap the partner sequence. The step of identifying an eligible consensus sequence read may further comprise determining whether a number of families corresponding to the eligible consensus sequence reads aligned with the targeted fusion reference sequence is greater than or equal to a minimum molecular count threshold. The step of identifying an eligible consensus sequence read may further comprise determining whether a read count is greater than or equal to a minimum read count threshold, wherein the read count is a sum of the numbers of sequence reads for the families corresponding to the eligible consensus sequence reads aligned with the targeted fusion reference sequence. A portion of the sequence alignments correspond to sequence reads may map to a control gene reference sequence, wherein the consensus compressed data further include consensus sequence reads and consensus sequence alignments corresponding to the control gene reference sequence. The method may further comprise determining a presence of a process control target corresponding to the control gene reference sequence when a family count is greater than a minimum molecular count threshold and a read count is greater than a read count threshold, wherein the family count is the number of families corresponding to the consensus sequence reads aligned with the control gene reference sequence and the read count is a sum of the numbers of sequence reads for the corresponding families. The fusion may comprise an intergenic fusion and the targeted fusion reference sequence may comprise a reference sequence for the fusion of two genes at a fusion breakpoint. The fusion may comprise an intragenic fusion and the targeted fusion reference sequence may comprise a reference sequence for the fusion of two exons at a fusion breakpoint within a same gene. A portion of the consensus sequence alignments may correspond to consensus sequence reads aligned with one or more wild type reference sequences for the same gene. For intragenic fusions, the step for detecting a fusion further may further comprise calculating a ratio of a read count for the intragenic fusion to a mean read count corresponding to the consensus sequence reads aligned with the wild type reference sequences for the same gene. For intragenic fusions, the step for detecting a fusion further may further comprise calculating a ratio of a read count for the intragenic fusion to a sum of read counts corresponding to the consensus sequence reads aligned with the wild type reference sequences and the consensus sequence reads aligned with the targeted fusion reference sequences for the same gene. A portion of the consensus sequence reads may partially map to the targeted fusion reference sequences. The step of detecting a fusion may further comprise detecting a non-targeted fusion based on partially mapped consensus sequence reads.

According to an exemplary embodiment, there is provided a system for compressing molecular tagged nucleic acid sequence data for fusion detection, comprising a machine-readable memory and a processor in communication with the memory, wherein the processor is configured to execute machine-readable instructions, which, when executed by the processor, cause the system to perform a method comprising (a) receiving a plurality of nucleic acid sequence reads and a plurality of sequence alignments for a plurality of families of sequence reads, wherein each sequence read is associated with a molecular tag sequence, the molecular tag sequence identifying a family of sequence reads resulting from a particular polynucleotide molecule in a nucleic acid sample, each family having a number of sequence reads, wherein a portion of the sequence alignments correspond to sequence reads mapped to a targeted fusion reference sequence; (b) determining a consensus sequence read for each family of sequence reads based on flow space signal measurements corresponding to the sequence reads for the family; (c) determining a consensus sequence alignment for each family of sequence reads, wherein a portion of the consensus sequence alignments correspond to the consensus sequence reads aligned with the targeted fusion reference sequence; (d) generating a compressed data structure comprising consensus compressed data, the consensus compressed data including the consensus sequence read and the consensus sequence alignment for each family; and (e) detecting a fusion using the consensus sequence reads and the consensus sequence alignments from the compressed data structure. The method may further comprise, for bidirectional sequencing wherein a forward consensus sequence read and a reverse consensus sequence read are in separate families, where a forward family is associated with a first prefix tag and a first suffix tag and a reverse family is associated with a second prefix tag and a second suffix tag, combining the forward and reverse families when a reverse complement of the second prefix tag and second suffix tag matches the first prefix tag and the first suffix tag to form a combined family having one consensus sequence read for the compressed data structure. The step of detecting a fusion may further comprise identifying an eligible consensus sequence read based on characteristics of the consensus sequence alignment of the consensus sequence read with the targeted fusion reference sequence. The characteristics may include a homology characteristic, a mapping quality characteristic and a breakpoint spanning characteristic. The step of identifying an eligible consensus sequence read may further comprise determining whether the consensus sequence read aligned with the targeted fusion reference sequence spans a fusion breakpoint of the targeted fusion reference sequence. The step of identifying an eligible consensus sequence read may further comprise determining whether first and second homology levels of the consensus sequence read with first and second partner sequences, respectively, of the targeted fusion reference sequence are greater than or equal to a minimum homology threshold. The step of identifying an eligible consensus sequence read may further comprise determining whether first and second mapping quality values for the consensus sequence read within first and second partner sequences, respectively, of the targeted fusion reference sequence are greater than or equal to a mapping quality threshold. The step of identifying an eligible consensus sequence read may further comprise determining the mapping quality value by calculating a ratio of a number of matching bases in the consensus sequence read that match the partner sequence to a number of overlapping bases in the consensus sequence read that overlap the partner sequence. The step of identifying an eligible consensus sequence read may further comprise determining whether a number of families corresponding to the eligible consensus sequence reads aligned with the targeted fusion reference sequence is greater than or equal to a minimum molecular count threshold. The step of identifying an eligible consensus sequence read may further comprise determining whether a read count is greater than or equal to a minimum read count threshold, wherein the read count is a sum of the numbers of sequence reads for the families corresponding to the eligible consensus sequence reads aligned with the targeted fusion reference sequence. A portion of the sequence alignments correspond to sequence reads may map to a control gene reference sequence, wherein the consensus compressed data further include consensus sequence reads and consensus sequence alignments corresponding to the control gene reference sequence. The method may further comprise determining a presence of a process control target corresponding to the control gene reference sequence when a family count is greater than a minimum molecular count threshold and a read count is greater than a read count threshold, wherein the family count is the number of families corresponding to the consensus sequence reads aligned with the control gene reference sequence and the read count is a sum of the numbers of sequence reads for the corresponding families. The fusion may comprise an intergenic fusion and the targeted fusion reference sequence may comprise a reference sequence for the fusion of two genes at a fusion breakpoint. The fusion may comprise an intragenic fusion and the targeted fusion reference sequence may comprise a reference sequence for the fusion of two exons at a fusion breakpoint within a same gene. A portion of the consensus sequence alignments may correspond to consensus sequence reads aligned with one or more wild type reference sequences for the same gene. For intragenic fusions, the step for detecting a fusion further may further comprise calculating a ratio of a read count for the intragenic fusion to a mean read count corresponding to the consensus sequence reads aligned with the wild type reference sequences for the same gene. For intragenic fusions, the step for detecting a fusion further may further comprise calculating a ratio of a read count for the intragenic fusion to a sum of read counts corresponding to the consensus sequence reads aligned with the wild type reference sequences and the consensus sequence reads aligned with the targeted fusion reference sequences for the same gene. A portion of the consensus sequence reads may partially map to the targeted fusion reference sequences. The step of detecting a fusion may further comprise detecting a non-targeted fusion based on partially mapped consensus sequence reads.

According to an exemplary embodiment, there is provided a non-transitory machine-readable storage medium comprising instructions which, when executed by a processor, cause the processor to perform a method for compressing molecular tagged nucleic acid sequence data for fusion detection, comprising (a) receiving a plurality of nucleic acid sequence reads and a plurality of sequence alignments for a plurality of families of sequence reads, wherein each sequence read is associated with a molecular tag sequence, the molecular tag sequence identifying a family of sequence reads resulting from a particular polynucleotide molecule in a nucleic acid sample, each family having a number of sequence reads, wherein a portion of the sequence alignments correspond to sequence reads mapped to a targeted fusion reference sequence; (b) determining a consensus sequence read for each family of sequence reads based on flow space signal measurements corresponding to the sequence reads for the family; (c) determining a consensus sequence alignment for each family of sequence reads, wherein a portion of the consensus sequence alignments correspond to the consensus sequence reads aligned with the targeted fusion reference sequence; (d) generating a compressed data structure comprising consensus compressed data, the consensus compressed data including the consensus sequence read and the consensus sequence alignment for each family; and (e) detecting a fusion using the consensus sequence reads and the consensus sequence alignments from the compressed data structure. The method may further comprise, for bidirectional sequencing wherein a forward consensus sequence read and a reverse consensus sequence read are in separate families, where a forward family is associated with a first prefix tag and a first suffix tag and a reverse family is associated with a second prefix tag and a second suffix tag, combining the forward and reverse families when a reverse complement of the second prefix tag and second suffix tag matches the first prefix tag and the first suffix tag to form a combined family having one consensus sequence read for the compressed data structure. The step of detecting a fusion may further comprise identifying an eligible consensus sequence read based on characteristics of the consensus sequence alignment of the consensus sequence read with the targeted fusion reference sequence. The characteristics may include a homology characteristic, a mapping quality characteristic and a breakpoint spanning characteristic. The step of identifying an eligible consensus sequence read may further comprise determining whether the consensus sequence read aligned with the targeted fusion reference sequence spans a fusion breakpoint of the targeted fusion reference sequence. The step of identifying an eligible consensus sequence read may further comprise determining whether first and second homology levels of the consensus sequence read with first and second partner sequences, respectively, of the targeted fusion reference sequence are greater than or equal to a minimum homology threshold. The step of identifying an eligible consensus sequence read may further comprise determining whether first and second mapping quality values for the consensus sequence read within first and second partner sequences, respectively, of the targeted fusion reference sequence are greater than or equal to a mapping quality threshold. The step of identifying an eligible consensus sequence read may further comprise determining the mapping quality value by calculating a ratio of a number of matching bases in the consensus sequence read that match the partner sequence to a number of overlapping bases in the consensus sequence read that overlap the partner sequence. The step of identifying an eligible consensus sequence read may further comprise determining whether a number of families corresponding to the eligible consensus sequence reads aligned with the targeted fusion reference sequence is greater than or equal to a minimum molecular count threshold. The step of identifying an eligible consensus sequence read may further comprise determining whether a read count is greater than or equal to a minimum read count threshold, wherein the read count is a sum of the numbers of sequence reads for the families corresponding to the eligible consensus sequence reads aligned with the targeted fusion reference sequence. A portion of the sequence alignments correspond to sequence reads may map to a control gene reference sequence, wherein the consensus compressed data further include consensus sequence reads and consensus sequence alignments corresponding to the control gene reference sequence. The method may further comprise determining a presence of a process control target corresponding to the control gene reference sequence when a family count is greater than a minimum molecular count threshold and a read count is greater than a read count threshold, wherein the family count is the number of families corresponding to the consensus sequence reads aligned with the control gene reference sequence and the read count is a sum of the numbers of sequence reads for the corresponding families. The fusion may comprise an intergenic fusion and the targeted fusion reference sequence may comprise a reference sequence for the fusion of two genes at a fusion breakpoint. The fusion may comprise an intragenic fusion and the targeted fusion reference sequence may comprise a reference sequence for the fusion of two exons at a fusion breakpoint within a same gene. A portion of the consensus sequence alignments may correspond to consensus sequence reads aligned with one or more wild type reference sequences for the same gene. For intragenic fusions, the step for detecting a fusion further may further comprise calculating a ratio of a read count for the intragenic fusion to a mean read count corresponding to the consensus sequence reads aligned with the wild type reference sequences for the same gene. For intragenic fusions, the step for detecting a fusion further may further comprise calculating a ratio of a read count for the intragenic fusion to a sum of read counts corresponding to the consensus sequence reads aligned with the wild type reference sequences and the consensus sequence reads aligned with the targeted fusion reference sequences for the same gene. A portion of the consensus sequence reads may partially map to the targeted fusion reference sequences. The step of detecting a fusion may further comprise detecting a non-targeted fusion based on partially mapped consensus sequence reads.

Nucleic acid sequence data can be generated using various techniques, platforms or technologies, including, but not limited to: capillary electrophoresis, microarrays, ligation-based systems, polymerase-based systems, hybridization-based systems, direct or indirect nucleotide identification systems, pyrosequencing, ion- or pH-based detection systems, electronic signature-based systems, etc.

Figure 8:
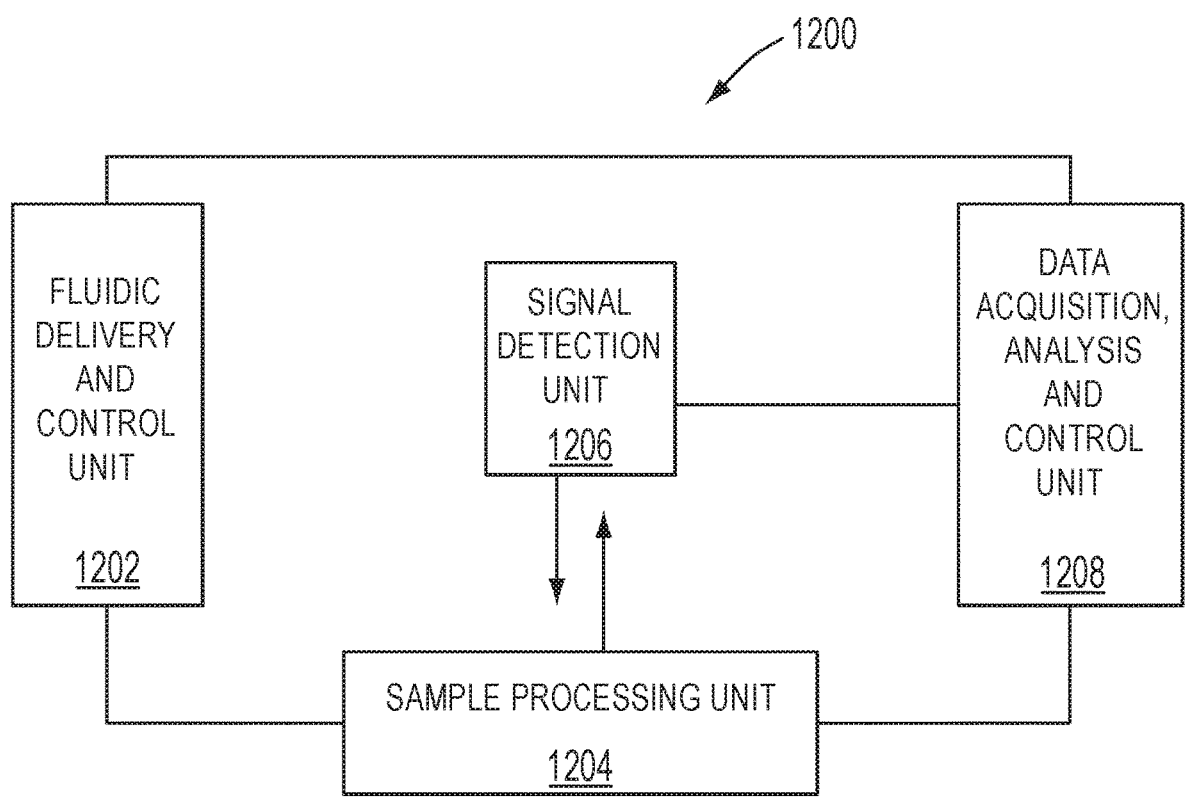
FIG. 8 is a block diagram of an exemplary system for nucleic acid sequencing, in accordance with an embodiment.

Various embodiments of nucleic acid sequencing platforms, such as a nucleic acid sequencer, can include components as displayed in the block diagram of FIG. 8. According to various embodiments, sequencing instrument 1200 can include a fluidic delivery and control unit 1202, a sample processing unit 1204, a signal detection unit 1206, and a data acquisition, analysis and control unit 1208. Various embodiments of instrumentation, reagents, libraries and methods used for next generation sequencing are described in U.S. Patent Application Publication No. 2009/0127589 and No. 2009/0026082. Various embodiments of instrument 1200 can provide for automated sequencing that can be used to gather sequence information from a plurality of sequences in parallel, such as substantially simultaneously.

In various embodiments, the fluidics delivery and control unit 1202 can include reagent delivery system. The reagent delivery system can include a reagent reservoir for the storage of various reagents. The reagents can include RNA-based primers, forward/reverse DNA primers, oligonucleotide mixtures for ligation sequencing, nucleotide mixtures for sequencing-by-synthesis, optional ECC oligonucleotide mixtures, buffers, wash reagents, blocking reagent, stripping reagents, and the like. Additionally, the reagent delivery system can include a pipetting system or a continuous flow system which connects the sample processing unit with the reagent reservoir.

In various embodiments, the sample processing unit 1204 can include a sample chamber, such as flow cell, a substrate, a micro-array, a multi-well tray, or the like. The sample processing unit 1204 can include multiple lanes, multiple channels, multiple wells, or other means of processing multiple sample sets substantially simultaneously. Additionally, the sample processing unit can include multiple sample chambers to enable processing of multiple runs simultaneously. In particular embodiments, the system can perform signal detection on one sample chamber while substantially simultaneously processing another sample chamber. Additionally, the sample processing unit can include an automation system for moving or manipulating the sample chamber.

In various embodiments, the signal detection unit 1206 can include an imaging or detection sensor. For example, the imaging or detection sensor can include a CCD, a CMOS, an ion or chemical sensor, such as an ion sensitive layer overlying a CMOS or FET, a current or voltage detector, or the like. The signal detection unit 1206 can include an excitation system to cause a probe, such as a fluorescent dye, to emit a signal. The excitation system can include an illumination source, such as arc lamp, a laser, a light emitting diode (LED), or the like. In particular embodiments, the signal detection unit 1206 can include optics for the transmission of light from an illumination source to the sample or from the sample to the imaging or detection sensor. Alternatively, the signal detection unit 1206 may provide for electronic or non-photon based methods for detection and consequently not include an illumination source. In various embodiments, electronic-based signal detection may occur when a detectable signal or species is produced during a sequencing reaction. For example, a signal can be produced by the interaction of a released byproduct or moiety, such as a released ion, such as a hydrogen ion, interacting with an ion or chemical sensitive layer. In other embodiments a detectable signal may arise as a result of an enzymatic cascade such as used in pyrosequencing (see, for example, U.S. Patent Application Publication No. 2009/0325145) where pyrophosphate is generated through base incorporation by a polymerase which further reacts with ATP sulfurylase to generate ATP in the presence of adenosine 5' phosphosulfate wherein the ATP generated may be consumed in a luciferase mediated reaction to generate a chemiluminescent signal. In another example, changes in an electrical current can be detected as a nucleic acid passes through a nanopore without the need for an illumination source.

In various embodiments, a data acquisition analysis and control unit 1208 can monitor various system parameters. The system parameters can include temperature of various portions of instrument 1200, such as sample processing unit or reagent reservoirs, volumes of various reagents, the status of various system subcomponents, such as a manipulator, a stepper motor, a pump, or the like, or any combination thereof.

It will be appreciated by one skilled in the art that various embodiments of instrument 1200 can be used to practice variety of sequencing methods including ligation-based methods, sequencing by synthesis, single molecule methods, nanopore sequencing, and other sequencing techniques.

In various embodiments, the sequencing instrument 1200 can determine the sequence of a nucleic acid, such as a polynucleotide or an oligonucleotide. The nucleic acid can include DNA or RNA, and can be single stranded, such as ssDNA and RNA, or double stranded, such as dsDNA or a RNA/cDNA pair. In various embodiments, the nucleic acid can include or be derived from a fragment library, a mate pair library, a ChIP fragment, or the like. In particular embodiments, the sequencing instrument 1200 can obtain the sequence information from a single nucleic acid molecule or from a group of substantially identical nucleic acid molecules.

In various embodiments, sequencing instrument 1200 can output nucleic acid sequencing read data in a variety of different output data file types/formats, including, but not limited to: *.fasta, *.csfasta, *seq.txt, *qseq.txt, *.fastq, *.sff, *prb.txt, *.sms, *srs and/or *.qv.

According to various exemplary embodiments, one or more features of any one or more of the above-discussed teachings and/or exemplary embodiments may be performed or implemented using appropriately configured and/or programmed hardware and/or software elements. Determining whether an embodiment is implemented using hardware and/or software elements may be based on any number of factors, such as desired computational rate, power levels, heat tolerances, processing cycle budget, input data rates, output data rates, memory resources, data bus speeds, etc., and other design or performance constraints.

Examples of hardware elements may include processors, microprocessors, input(s) and/or output(s) (I/O) device(s) (or peripherals) that are communicatively coupled via a local interface circuit, circuit elements (e.g., transistors, resistors, capacitors, inductors, and so forth), integrated circuits, application specific integrated circuits (ASIC), programmable logic devices (PLD), digital signal processors (DSP), field programmable gate array (FPGA), logic gates, registers, semiconductor device, chips, microchips, chip sets, and so forth. The local interface may include, for example, one or more buses or other wired or wireless connections, controllers, buffers (caches), drivers, repeaters and receivers, etc., to allow appropriate communications between hardware components. A processor is a hardware device for executing software, particularly software stored in memory. The processor can be any custom made or commercially available processor, a central processing unit (CPU), an auxiliary processor among several processors associated with the computer, a semiconductor based microprocessor (e.g., in the form of a microchip or chip set), a macroprocessor, or generally any device for executing software instructions. A processor can also represent a distributed processing architecture. The I/O devices can include input devices, for example, a keyboard, a mouse, a scanner, a microphone, a touch screen, an interface for various medical devices and/or laboratory instruments, a bar code reader, a stylus, a laser reader, a radio-frequency device reader, etc. Furthermore, the I/O devices also can include output devices, for example, a printer, a bar code printer, a display, etc. Finally, the I/O devices further can include devices that communicate as both inputs and outputs, for example, a modulator/demodulator (modem; for accessing another device, system, or network), a radio frequency (RF) or other transceiver, a telephonic interface, a bridge, a router, etc.

Examples of software may include software components, programs, applications, computer programs, application programs, system programs, machine programs, operating system software, middleware, firmware, software modules, routines, subroutines, functions, methods, procedures, software interfaces, application program interfaces (API), instruction sets, computing code, computer code, code segments, computer code segments, words, values, symbols, or any combination thereof. A software in memory may include one or more separate programs, which may include ordered listings of executable instructions for implementing logical functions. The software in memory may include a system for identifying data streams in accordance with the present teachings and any suitable custom made or commercially available operating system (O/S), which may control the execution of other computer programs such as the system, and provides scheduling, input-output control, file and data management, memory management, communication control, etc.

According to various exemplary embodiments, one or more features of any one or more of the above-discussed teachings and/or exemplary embodiments may be performed or implemented using appropriately configured and/or programmed non-transitory machine-readable medium or article that may store an instruction or a set of instructions that, if executed by a machine, may cause the machine to perform a method and/or operations in accordance with the exemplary embodiments. Such a machine may include, for example, any suitable processing platform, computing platform, computing device, processing device, computing system, processing system, computer, processor, scientific or laboratory instrument, etc., and may be implemented using any suitable combination of hardware and/or software. The machine-readable medium or article may include, for example, any suitable type of memory unit, memory device, memory article, memory medium, storage device, storage article, storage medium and/or storage unit, for example, memory, removable or non-removable media, erasable or non-erasable media, writeable or re-writeable media, digital or analog media, hard disk, floppy disk, read-only memory compact disc (CD-ROM), recordable compact disc (CD-R), rewriteable compact disc (CD-RW), optical disk, magnetic media, magneto-optical media, removable memory cards or disks, various types of Digital Versatile Disc (DVD), a tape, a cassette, etc., including any medium suitable for use in a computer. Memory can include any one or a combination of volatile memory elements (e.g., random access memory (RAM, such as DRAM, SRAM, SDRAM, etc.)) and non-volatile memory elements (e.g., ROM, EPROM, EEROM, Flash memory, hard drive, tape, CDROM, etc.). Moreover, memory can incorporate electronic, magnetic, optical, and/or other types of storage media. Memory can have a distributed architecture where various components are situated remote from one another, but are still accessed by the processor. The instructions may include any suitable type of code, such as source code, compiled code, interpreted code, executable code, static code, dynamic code, encrypted code, etc., implemented using any suitable high-level, low-level, object-oriented, visual, compiled and/or interpreted programming language.

According to various exemplary embodiments, one or more features of any one or more of the above-discussed teachings and/or exemplary embodiments may be performed or implemented at least partly using a distributed, clustered, remote, or cloud computing resource.

According to various exemplary embodiments, one or more features of any one or more of the above-discussed teachings and/or exemplary embodiments may be performed or implemented using a source program, executable program (object code), script, or any other entity comprising a set of instructions to be performed. When a source program, the program can be translated via a compiler, assembler, interpreter, etc., which may or may not be included within the memory, so as to operate properly in connection with the O/S. The instructions may be written using (a) an object oriented programming language, which has classes of data and methods, or (b) a procedural programming language, which has routines, subroutines, and/or functions, which may include, for example, C, C++, R, Pascal, Basic, Fortran, Cobol, Perl, Java, and Ada.

According to various exemplary embodiments, one or more of the above-discussed exemplary embodiments may include transmitting, displaying, storing, printing or outputting to a user interface device, a computer readable storage medium, a local computer system or a remote computer system, information related to any information, signal, data, and/or intermediate or final results that may have been generated, accessed, or used by such exemplary embodiments. Such transmitted, displayed, stored, printed or outputted information can take the form of searchable and/or filterable lists of runs and reports, pictures, tables, charts, graphs, spreadsheets, correlations, sequences, and combinations thereof, for example.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

---

---

What is claimed is:

1. A method for compressing molecular tagged nucleic acid sequence data for fusion detection, comprising:
   amplifying a nucleic acid sample in a presence of primers to produce a plurality of amplicons, the primers including a 5' primer and a 3' primer, the 5' primer and the 3' primer flanking a breakpoint region associated with a gene fusion, wherein a prefix tag is appended to the 5' primer and a suffix tag is appended to the 3' primer, the prefix tag and suffix tag comprising a unique molecular tag for a polynucleotide molecule in the nucleic acid sample;

sequencing the plurality of amplicons to generate a plurality of nucleic acid sequence reads;

mapping the nucleic acid sequence reads to a reference sequence to produce a plurality of sequence alignments, the reference sequence including a targeted fusion reference sequence;

receiving, at a processor, the plurality of nucleic acid sequence reads and the plurality of sequence alignments for a plurality of families of sequence reads, wherein each sequence read is associated with a molecular tag sequence, the molecular tag sequence identifying a family of sequence reads resulting from a particular polynucleotide molecule in the nucleic acid sample, each family having a number of sequence reads, wherein a portion of the sequence alignments corresponds to sequence reads mapped to the targeted fusion reference sequence;

determining a consensus sequence read for each family of sequence reads based on flow space signal measurements corresponding to the sequence reads for the family;

determining a consensus sequence alignment for each family of sequence reads, comprising selecting the sequence alignment having a highest mapping quality corresponding to the family of sequence reads and comparing the sequence read corresponding to the sequence alignment having the highest mapping quality to the consensus sequence read for the family, wherein a portion of the consensus sequence alignments corresponds to the consensus sequence reads aligned with the targeted fusion reference sequence;

generating a compressed data structure comprising consensus compressed data, the consensus compressed data including the consensus sequence read and the consensus sequence alignment for each family, wherein a data volume of the compressed data structure is less than an original data volume of the plurality of nucleic acid sequence reads and the plurality of sequence alignments;

storing the compressed data structure in a memory, wherein an amount of memory for the storing the compressed data structure is less than an original amount of memory for storing the plurality of nucleic acid sequence reads and the plurality of sequence alignments; and detecting a fusion using the consensus sequence reads and the consensus sequence alignments from the compressed data structure, wherein the detecting comprises identifying an eligible consensus sequence read based on characteristics of the consensus sequence alignment of the consensus sequence read with the targeted fusion reference sequence and determining whether a number of families corresponding to the eligible consensus sequence reads aligned with the targeted fusion reference sequence is greater than or equal to a minimum molecular count threshold.

2. The method of claim 1, wherein the sequence reads result from bidirectional sequencing, wherein a forward consensus sequence read and a reverse consensus sequence read are in separate families, including a forward family associated with a first prefix tag and a first suffix tag and a reverse family associated with a second prefix tag and a second suffix tag, the method further comprising combining the forward and reverse families when a reverse complement of the second prefix tag and second suffix tag matches the first prefix tag and the first suffix tag to form a combined family having one consensus sequence read for the compressed data structure.

3. The method of claim 1, wherein the characteristics include a homology characteristic, a mapping quality characteristic and a breakpoint spanning characteristic.

4. The method of claim 1, wherein the identifying an eligible consensus sequence read further comprises determining whether the consensus sequence read aligned with the targeted fusion reference sequence spans a fusion breakpoint of the targeted fusion reference sequence.

5. The method of claim 1, wherein the identifying an eligible consensus sequence read further comprises determining whether first and second homology levels of the consensus sequence read with first and second partner sequences, respectively, of the targeted fusion reference sequence are greater than or equal to a minimum homology threshold.

6. The method of claim 1, wherein the identifying an eligible consensus sequence read further comprises determining whether first and second mapping quality values for the consensus sequence read within first and second partner sequences, respectively, of the targeted fusion reference sequence are greater than or equal to a mapping quality threshold.

7. The method of claim 6, wherein the identifying an eligible consensus sequence read further comprises determining the mapping quality value by calculating a ratio of a number of matching bases in the consensus sequence read that match the partner sequence to a number of overlapping bases in the consensus sequence read that overlap the partner sequence.

8. The method of claim 1, wherein the detecting a fusion further comprises determining whether a read count is greater than or equal to a minimum read count threshold, wherein the read count is a sum of the numbers of sequence reads for the families corresponding to the eligible consensus sequence reads aligned with the targeted fusion reference sequence.

9. The method of claim 1, wherein a second portion of the sequence alignments correspond to sequence reads mapped to a control gene reference sequence, wherein the consensus compressed data further include consensus sequence reads and consensus sequence alignments corresponding to the control gene reference sequence.

10. The method of claim 9, further comprising determining a presence of a process control target corresponding to the control gene reference sequence when a family count is greater than the minimum molecular count threshold and a read count is greater than a read count threshold, wherein the family count is the number of families corresponding to the consensus sequence reads aligned with the control gene reference sequence and the read count is a sum of the numbers of sequence reads for the corresponding families.

11. The method of claim 1, wherein the fusion comprises an intergenic fusion and the targeted fusion reference sequence comprises a reference sequence for the fusion of two genes at a fusion breakpoint.

12. The method of claim 1, wherein the fusion comprises an intragenic fusion and the targeted fusion reference sequence comprises a reference sequence for the fusion of two exons at a fusion breakpoint within a same gene.

13. The method of claim 12, wherein a second portion of the consensus sequence alignments corresponds to the consensus sequence reads aligned with one or more wild type reference sequences for the same gene.

14. The method of claim 13, wherein the detecting a fusion further comprises calculating a ratio of a read count for the intragenic fusion to a mean read count corresponding to the consensus sequence reads aligned with the wild type reference sequences for the same gene.

15. The method of claim 13, wherein the detecting a fusion further comprises calculating a ratio of a read count for the intragenic fusion to a sum of read counts corresponding to the consensus sequence reads aligned with the wild type reference sequences and the consensus sequence reads aligned with the targeted fusion reference sequences for the same gene.

16. The method of claim 1, wherein a portion of the consensus sequence reads partially map to the targeted fusion reference sequences, wherein detecting a fusion further comprises detecting a non-targeted fusion based on partially mapped consensus sequence reads.

17. The method of claim 1, wherein the step of determining a consensus sequence alignment further comprises, choosing the sequence alignment having the highest mapping quality as the consensus sequence alignment for the family when the sequence read corresponding to the sequence alignment having the highest mapping quality matches the consensus sequence read for the family.

18. The method of claim 1, wherein the step of determining a consensus sequence alignment further comprises, aligning the consensus sequence read to the reference sequence including the targeted fusion reference sequence and a control gene reference sequence to determine the consensus sequence alignment for the family when the sequence read corresponding to the sequence alignment having the highest mapping quality does not match the consensus sequence read for the family.

19. A non-transitory machine-readable storage medium comprising instructions which, when executed by a processor, cause the processor to perform a method for compressing molecular tagged nucleic acid sequence data for fusion detection, comprising:
  receiving, at the processor, a plurality of nucleic acid sequence reads and a plurality of sequence alignments for a plurality of families of sequence reads, wherein each sequence read is associated with a molecular tag sequence, the molecular tag sequence identifying a family of sequence reads resulting from a particular polynucleotide molecule in a nucleic acid sample, each family having a number of sequence reads, wherein a portion of the sequence alignments corresponds to sequence reads mapped to a targeted fusion reference sequence, wherein the plurality of nucleic acid sequence reads are generated by amplifying the nucleic acid sample in a presence of primers to produce a plurality of amplicons, the primers including a 5' primer and a 3' primer, the 5' primer and the 3' primer flanking a breakpoint region associated with a gene fusion, wherein a prefix tag is appended to the 5' primer and a suffix tag is appended to the 3' primer, the prefix tag and suffix tag comprising a unique molecular tag for a polynucleotide molecule in the nucleic acid sample and sequencing the plurality of amplicons to generate the plurality of nucleic acid sequence reads, wherein the plurality of sequence alignments are generated by mapping the nucleic acid sequence reads to a reference sequence to produce the plurality of sequence alignments, the reference sequence including the targeted fusion reference sequence;
  determining a consensus sequence read for each family of sequence reads based on flow space signal measurements corresponding to the sequence reads for the family;
  determining a consensus sequence alignment for each family of sequence reads, comprising selecting the sequence alignment having a highest mapping quality corresponding to the family of sequence reads and comparing the sequence read corresponding to the sequence alignment having the highest mapping quality to the consensus sequence read for the family, wherein a portion of the consensus sequence alignments corresponds to the consensus sequence reads aligned with the targeted fusion reference sequence;
  generating a compressed data structure comprising consensus compressed data, the consensus compressed data including the consensus sequence read and the consensus sequence alignment for each family, wherein a data volume of the compressed data structure is less than an original data volume of the plurality of nucleic acid sequence reads and the plurality of sequence alignments;
  storing the compressed data structure in a memory, wherein an amount of memory for the storing the compressed data structure is less than an original amount of memory for storing the plurality of nucleic acid sequence reads and the plurality of sequence alignments; and
  detecting a fusion using the consensus sequence reads and the consensus sequence alignments from the compressed data structure, wherein the detecting comprises identifying an eligible consensus sequence read based on characteristics of the consensus sequence alignment of the consensus sequence read with the targeted fusion reference sequence and determining whether a number of families corresponding to the eligible consensus sequence reads aligned with the targeted fusion reference sequence is greater than or equal to a minimum molecular count threshold.

20. A system for compressing molecular tagged nucleic acid sequence data for fusion detection, comprising:
  a machine-readable memory; and
  a processor in communication with the memory, wherein the processor is configured to execute machine-readable instructions, which, when executed by the processor, cause the system to perform a method, comprising:
  receiving, at the processor, a plurality of nucleic acid sequence reads and a plurality of sequence alignments for a plurality of families of sequence reads, wherein each sequence read is associated with a molecular tag sequence, the molecular tag sequence identifying a family of sequence reads resulting from a particular polynucleotide molecule in a nucleic acid sample, each family having a number of sequence reads, wherein a portion of the sequence alignments corresponds to sequence reads mapped to a targeted fusion reference sequence, wherein the plurality of nucleic acid sequence reads are generated by amplifying the nucleic acid sample in a presence of primers to produce a plurality of amplicons, the primers including a 5' primer and a 3' primer, the 5' primer and the 3' primer flanking a breakpoint region associated with a gene fusion, wherein a prefix tag is appended to the 5' primer and a suffix tag is appended to the 3' primer, the prefix tag and suffix tag comprising a unique molecular tag for a polynucleotide molecule in the nucleic acid sample and sequencing the plurality of amplicons to generate the plurality of nucleic acid sequence reads, wherein the plurality of sequence alignments are generated by mapping the nucleic acid sequence reads to a reference sequence to produce the plurality of sequence alignments, the reference sequence including the targeted fusion reference sequence;

determining a consensus sequence read for each family of sequence reads based on flow space signal measurements corresponding to the sequence reads for the family;

determining a consensus sequence alignment for each family of sequence reads, comprising selecting the sequence alignment having a highest mapping quality corresponding to the family of sequence reads and comparing the sequence read corresponding to the sequence alignment having the highest mapping quality to the consensus sequence read for the family, wherein a portion of the consensus sequence alignments corresponds to the consensus sequence reads aligned with the targeted fusion reference sequence;

generating a compressed data structure comprising consensus compressed data, the consensus compressed data including the consensus sequence read and the consensus sequence alignment for each family, wherein a data volume of the compressed data structure is less than an original data volume of the plurality of nucleic acid sequence reads and the plurality of sequence alignments;

storing the compressed data structure in the memory, wherein an amount of memory for the storing the compressed data structure is less than an original amount of memory for storing the plurality of nucleic acid sequence reads and the plurality of sequence alignments; and detecting a fusion using the consensus sequence reads and the consensus sequence alignments from the compressed data structure, wherein the detecting comprises identifying an eligible consensus sequence read based on characteristics of the consensus sequence alignment of the consensus sequence read with the targeted fusion reference sequence and determining whether a number of families corresponding to the eligible consensus sequence reads aligned with the targeted fusion reference sequence is greater than or equal to a minimum molecular count threshold.

* * * * *

UNITED STATES PATENT AND TRADEMARK OFFICE
CERTIFICATE OF CORRECTION

| | | |
|---|---|---|
| PATENT NO. | : 11,894,105 B2 | Page 1 of 1 |
| APPLICATION NO. | : 16/136463 | |
| DATED | : February 6, 2024 | |
| INVENTOR(S) | : Rajesh Gottimukkala et al. | |

It is certified that error appears in the above-identified patent and that said Letters Patent is hereby corrected as shown below:

On the Title Page

In Column 1, item (54), in title, Line 3, delete "TAGGED NUCLEIC ACID" and insert -- TAGGED NUCLEIC ACID SEQUENCE DATA --, therefor.

In Column 1, item (72), in Inventors, Line 2, delete "Taipei" and insert -- Taipei City --, therefor.

In the Specification

In Column 1, in title, Line 3, delete "TAGGED NUCLEIC ACID" and insert -- TAGGED NUCLEIC ACID SEQUENCE DATA --, therefor.

Signed and Sealed this
Seventh Day of January, 2025

Derrick Brent
*Acting Director of the United States Patent and Trademark Office*